(12) United States Patent
Cadieux et al.

(10) Patent No.: US 8,742,109 B2
(45) Date of Patent: Jun. 3, 2014

(54) SYNTHETIC METHODS FOR SPIRO-OXINDOLE COMPOUNDS

(75) Inventors: Jean-Jacques Cadieux, Burnaby (CA); Mikhail Chafeev, Khimki (RU); Sultan Chowdhury, Surrey (CA); Jianmin Fu, Coquitlam (CA); Qi Jia, Burnaby (CA); Stefanie Abel, Thalwil (CH); Emad El-Sayed, Zumikon (CH); Elke Huthmann, Buchs (CH); Thomas Isarno, Niffer (FR)

(73) Assignee: Xenon Pharmaceuticals Inc., Burnaby, BC (CA)

( * ) Notice: Subject to any disclaimer, the term of this patent is extended or adjusted under 35 U.S.C. 154(b) by 0 days.

(21) Appl. No.: 13/620,391

(22) Filed: Sep. 14, 2012

(65) Prior Publication Data

US 2013/0072686 A1   Mar. 21, 2013

Related U.S. Application Data

(62) Division of application No. 12/904,880, filed on Oct. 14, 2010, now Pat. No. 8,445,696.

(60) Provisional application No. 61/251,335, filed on Oct. 14, 2009.

(51) Int. Cl.
*C07D 213/36* (2006.01)

(52) U.S. Cl.
USPC .......................................................... 546/15

(58) Field of Classification Search
USPC .......................................................... 546/15
See application file for complete search history.

(56) References Cited

U.S. PATENT DOCUMENTS

| | | | |
|---|---|---|---|
| 3,189,617 A | 6/1965 | Archer et al. |
| 3,723,459 A | 3/1973 | Paragamian |
| 3,845,770 A | 11/1974 | Theeuwes et al. |
| 4,045,576 A | 8/1977 | Welstead, Jr. et al. |
| 4,326,525 A | 4/1982 | Swanson et al. |
| 4,438,130 A | 3/1984 | Kaplan |
| 4,440,785 A | 4/1984 | Walsh |
| 4,670,566 A | 6/1987 | Walsh |
| 4,886,788 A | 12/1989 | Skuballa et al. |
| 4,935,446 A | 6/1990 | Imaki et al. |
| 5,023,265 A | 6/1991 | Scherlock et al. |
| 5,116,854 A | 5/1992 | Marfat |
| 5,182,289 A | 1/1993 | Ting et al. |
| 5,278,162 A | 1/1994 | Wilkerson |
| 5,296,478 A | 3/1994 | Teleha |
| 5,304,121 A | 4/1994 | Sahatjian |
| 5,453,516 A | 9/1995 | Fischer et al. |
| 5,663,431 A | 9/1997 | Di Malta et al. |
| 5,686,624 A | 11/1997 | Di Malta et al. |
| 5,696,145 A | 12/1997 | Foulon et al. |
| 5,723,625 A | 3/1998 | Keplinger et al. |
| 5,726,322 A | 3/1998 | Di Malta et al. |
| 5,728,723 A | 3/1998 | Di Malta et al. |
| 5,763,471 A | 6/1998 | Fourtillan et al. |
| 5,767,128 A | 6/1998 | Guillaumet et al. |
| 5,776,936 A | 7/1998 | Lee et al. |
| 5,849,780 A | 12/1998 | Di Malta et al. |
| 5,886,026 A | 3/1999 | Hunter et al. |
| 5,994,350 A | 11/1999 | Foulon et al. |
| 6,046,341 A | 4/2000 | Foulon et al. |
| 6,090,818 A | 7/2000 | Foulon et al. |
| 6,099,562 A | 8/2000 | Ding et al. |
| 6,110,969 A | 8/2000 | Tani et al. |
| 6,225,347 B1 | 5/2001 | Buchmann et al. |
| 6,235,780 B1 | 5/2001 | Ohuchida et al. |
| 6,262,293 B1 | 7/2001 | Tani et al. |
| 6,288,119 B1 | 9/2001 | Ohuchida et al. |
| 6,355,627 B1 | 3/2002 | Ishida et al. |
| 6,414,153 B1 | 7/2002 | Kelly et al. |
| 6,670,357 B2 | 12/2003 | Leftheris et al. |
| 6,964,973 B2 | 11/2005 | Zhi et al. |
| 7,368,470 B2 | 5/2008 | Sundermann et al. |
| 7,700,641 B2 | 4/2010 | Chafeev et al. |
| 7,799,798 B2 | 9/2010 | Chafeev et al. |
| 7,935,721 B2 | 5/2011 | Sun et al. |
| 8,101,647 B2 | 1/2012 | Chafeev et al. |
| 8,106,087 B2 | 1/2012 | Chafeev et al. |
| 8,263,606 B2 | 9/2012 | Chafeev et al. |
| 2002/0039790 A1 | 4/2002 | Keplinger et al. |
| 2004/0038970 A1 | 2/2004 | Thurieau et al. |
| 2004/0167224 A1 | 8/2004 | Ozaki et al. |

(Continued)

FOREIGN PATENT DOCUMENTS

| | | |
|---|---|---|
| CA | 2095718 A1 | 5/1992 |
| CA | 2107348 A1 | 7/1993 |

(Continued)

OTHER PUBLICATIONS

Adams et al., "Bicyclic N-Hydroxyurea Inhibitors of 5-Lipoxygenase: Pharmacodynamic, Pharmacokinetic, and in Vitro Metabolic Studies Characterizing *N*-Hydroxy-*N*-(2,3-dihydro-6-(phenylmethoxy)-3-benzofuranyl)urea," *J. Med. Chem.* 39(26): 5035-5046, 1996.

Akai, "Development of Novel Asymmetric Reactions Oriented to Next-Generation Enzymatic Organic Syntheses," *Yakugaku Zasshi* 123(11): 919-931, 2003.

Al-Thebeiti and El-Zohry, "A Facile Route for the Synthesis of Some New Spiro[indoline-3,3'-indan]-2,1'-dione Derivatives," *Heterocycles* 41(11): 2475-2480, 1995.

Alabaster et al., "The Synthesis of 5-Substituted 2,3-Dihydrobenzofurans," *Synthesis* 12: 950-952, Dec. 1988.

Alcaide et al., "Efficient Entry to Diversely Functionalized Spirocyclic Oxindoles from Isatins through Carbonyl-Addition/Cyclization Reaction Sequences," *J. Org. Chem.* 71(6): 2346-2351, 2006.

(Continued)

*Primary Examiner* — Shawquia Young
(74) *Attorney, Agent, or Firm* — Seed IP Law Group PLLC

(57) ABSTRACT

This invention is directed to methods of preparing certain spiro-oxindole derivatives, which are useful for the treatment and/or prevention of sodium channel-mediated diseases or conditions, such as pain.

6 Claims, No Drawings

(56) References Cited

U.S. PATENT DOCUMENTS

| | | |
|---|---|---|
| 2005/0004137 A1 | 1/2005 | Romano |
| 2005/0004138 A1 | 1/2005 | Romano |
| 2005/0014764 A1 | 1/2005 | Romano et al. |
| 2005/0020617 A1 | 1/2005 | Bastian et al. |
| 2005/0038036 A1 | 2/2005 | Romano et al. |
| 2005/0075351 A1 | 4/2005 | Berg et al. |
| 2005/0153998 A1 | 7/2005 | Ito et al. |
| 2005/0159473 A1 | 7/2005 | Sall et al. |
| 2005/0171186 A1 | 8/2005 | Fensome et al. |
| 2005/0256110 A1 | 11/2005 | Collins et al. |
| 2005/0256144 A1 | 11/2005 | Kath et al. |
| 2006/0247441 A1 | 11/2006 | Wilk |
| 2007/0049609 A1 | 3/2007 | Broka et al. |
| 2007/0072831 A1 | 3/2007 | Cai et al. |
| 2007/0105820 A1 | 5/2007 | Chafeev et al. |
| 2007/0299102 A1 | 12/2007 | Felding et al. |
| 2008/0103151 A9 | 5/2008 | Chafeev et al. |
| 2010/0137299 A1* | 6/2010 | Chafeev et al. ............ 514/232.8 |
| 2010/0331386 A1 | 12/2010 | Chafeev et al. |
| 2011/0034500 A1 | 2/2011 | Chafeev et al. |
| 2011/0086899 A1 | 4/2011 | Winters et al. |
| 2011/0087027 A1 | 4/2011 | Cadieux et al. |
| 2011/0172282 A9 | 7/2011 | Chafeev et al. |
| 2011/0237567 A9 | 9/2011 | Chafeev et al. |
| 2011/0269788 A1 | 11/2011 | Cadieux et al. |
| 2011/0294842 A9 | 12/2011 | Cadieux et al. |
| 2012/0122909 A9 | 5/2012 | Chafeev et al. |
| 2012/0295897 A1 | 11/2012 | Chafeev et al. |
| 2013/0072537 A1 | 3/2013 | Chafeev et al. |
| 2013/0143941 A1 | 6/2013 | Winters et al. |
| 2013/0252962 A1 | 9/2013 | Chafeev et al. |
| 2013/0274483 A1 | 10/2013 | Sun et al. |

FOREIGN PATENT DOCUMENTS

| | | | |
|---|---|---|---|
| CA | 2129215 A1 | 1/1995 | |
| CA | 2274898 A1 | 6/1998 | |
| CA | 2450550 A1 | 1/2003 | |
| CA | 2466915 A1 | 8/2003 | |
| CA | 2487494 A1 | 12/2003 | |
| CA | 2235686 C | 6/2007 | |
| DE | 1956237 A | 5/1971 | |
| DE | 2113343 A1 | 9/1972 | |
| EP | 0147805 A2 | 7/1985 | |
| EP | 0164860 A1 | 12/1985 | |
| EP | 0175551 A1 | 3/1986 | |
| EP | 0608058 A1 | 7/1994 | |
| EP | 1422217 A2 | 5/2004 | |
| EP | 1557166 A1 | 7/2005 | |
| EP | 2073806 B1 | 2/2012 | |
| FR | 2722195 A1 | 1/1996 | |
| JP | 1095766 A | 4/1998 | |
| JP | 2003505388 | 2/2003 | |
| WO | WO 86/03749 A1 | 7/1986 | |
| WO | WO 91/01306 A1 | 2/1991 | |
| WO | WO 91/04974 A1 | 4/1991 | |
| WO | WO 91/06545 A1 | 5/1991 | |
| WO | WO 92/09577 A1 | 6/1992 | |
| WO | WO 93/12786 A1 | 7/1993 | |
| WO | WO 93/15051 A1 | 8/1993 | |
| WO | WO 94/03427 A1 | 2/1994 | |
| WO | WO 95/06688 A1 | 3/1995 | |
| WO | WO 95/14667 A1 | 6/1995 | |
| WO | WO 97/15556 A1 | 5/1997 | |
| WO | WO 97/36895 A1 | 10/1997 | |
| WO | WO 98/25901 A1 | 6/1998 | |
| WO | WO 98/50016 A2 | 11/1998 | |
| WO | WO 00/06556 A1 | 2/2000 | |
| WO | WO 00/71129 A1 | 11/2000 | |
| WO | WO 01/05790 A1 | 1/2001 | |
| WO | WO 01/38564 A2 | 5/2001 | |
| WO | WO 01/38564 A3 | 5/2001 | |
| WO | WO 01/74775 A1 | 10/2001 | |
| WO | WO 02/30868 A1 | 4/2002 | |
| WO | WO 02/38544 A2 | 5/2002 | |
| WO | WO 03/000677 A1 | 1/2003 | |
| WO | WO 03/037274 A2 | 5/2003 | |
| WO | WO 03/037890 A2 | 5/2003 | |
| WO | WO 03/064425 A1 | 8/2003 | |
| WO | WO 03/078394 A1 | 9/2003 | |
| WO | WO 03/106457 A1 | 12/2003 | |
| WO | WO 04/000225 A2 | 12/2003 | |
| WO | WO 04/000227 A2 | 12/2003 | |
| WO | WO 2004/048320 A1 | 6/2004 | |
| WO | WO 2005/011657 A2 | 2/2005 | |
| WO | WO 2005/016913 A1 | 2/2005 | |
| WO | WO 2005/019208 A1 | 3/2005 | |
| WO | WO 2005/035498 A1 | 4/2005 | |
| WO | WO 2005/092304 A2 | 10/2005 | |
| WO | WO 2005/092895 A2 | 10/2005 | |
| WO | WO 2005/097107 A2 | 10/2005 | |
| WO | WO 2005/097122 A2 | 10/2005 | |
| WO | WO 2005/097136 A1 | 10/2005 | |
| WO | WO 2005/099689 A1 | 10/2005 | |
| WO | WO 2005/104711 A2 | 11/2005 | |
| WO | WO 2005/105753 A2 | 11/2005 | |
| WO | WO 2005/110992 A1 | 11/2005 | |
| WO | WO 2005/111024 A1 | 11/2005 | |
| WO | WO 2006/012173 A1 | 2/2006 | |
| WO | WO 2006/017075 A1 | 2/2006 | |
| WO | WO 2006/023107 A1 | 3/2006 | |
| WO | WO 2006/023109 A1 | 3/2006 | |
| WO | WO 2006/049290 A1 | 5/2006 | |
| WO | WO 2006/055752 A2 | 5/2006 | |
| WO | WO 2006/087019 A1 | 8/2006 | |
| WO | WO 2006/091646 A2 | 8/2006 | |
| WO | WO 2006/110654 A1 | 10/2006 | |
| WO | WO 2006/110917 A2 | 10/2006 | |
| WO | WO 2006/113864 A2 | 10/2006 | |
| WO | WO 2006/113875 A2 | 10/2006 | |
| WO | WO 2007/025925 A1 | 3/2007 | |
| WO | WO 2008/046046 A1 | 4/2008 | |
| WO | WO 2008/046049 A1 | 4/2008 | |
| WO | WO 2008/046065 A1 | 4/2008 | |
| WO | WO 2008/046082 A2 | 4/2008 | |
| WO | WO 2008/046083 A2 | 4/2008 | |
| WO | WO 2008/046084 A2 | 4/2008 | |
| WO | WO 2008/046087 A2 | 4/2008 | |
| WO | WO 2008/060789 A2 | 5/2008 | |
| WO | WO 2008/117050 A1 | 10/2008 | |
| WO | WO 2010/045197 A1 | 4/2010 | |
| WO | WO 2010/045251 A1 | 4/2010 | |
| WO | WO 2010/053998 A1 | 5/2010 | |
| WO | WO 2010/078307 A1 | 7/2010 | |
| WO | WO 2010/132352 A2 | 11/2010 | |
| WO | WO 2011/002708 A1 | 1/2011 | |
| WO | WO 2011/047173 A2 | 4/2011 | |
| WO | WO 2011/047174 A1 | 4/2011 | |
| WO | WO 2011/106729 A2 | 9/2011 | |
| WO | WO 2013/154712 A1 | 10/2013 | |

OTHER PUBLICATIONS

Alper et al., "Eine neuartige Methode zur Synthese von Spiro[pyrrolidin-3,3'-oxindolen]: katalysierte Ringerweiterung von Cyclopropanen mit Aldiminen," *Angew. Chem.* 111(21): 3379-3381, 1999.

Alper et al., "Facile, Novel Methodology for the Synthesis of Spiro[pyrrolidin-3,3'-oxindoles]: Catalyzed Ring Expansion Reactions of Cyclopropanes by Aldimines," *Angew. Chem. Int. Ed.* 38(21): 3186-3189, 1999.

Anger et al., "Medicinal Chemistry of Neuronal Voltage-Gated Sodium Channel Blockers," *Journal of Medicinal Chemistry* 44(2): 115-137, Jan. 18, 2001.

Arcangeli et al., "Targeting Ion Channels in Cancer: A Novel Frontier in Antineoplastic Therapy," *Current Medicinal Chemistry* 16: 66-93, 2009.

Autrey and Tahk, "The Synthesis and Stereochemistry of Some Isatylideneacetic Acid Derivatives," *Tetrahedron* 23: 901-917, 1967.

Bacher et al., "Oxindole alkaloids from *Uncaria tomentosa* induce apoptosis in proliferating, G0/G1-arrested and bc1-2-expressing acute lymphoblastic leukaemia cells," *British Journal of Haematology* 132: 615-622, 2005.

(56) References Cited

OTHER PUBLICATIONS

Banfi et al., "High Diastereoface Selection in an Ester Enolate Addition to α-Alkoxy Aldehydes: Stereoselective Synthesis of α-Methylene-β-hydroxy-γ-alkoxy Esters," *J. Org. Chem.* 49: 3784-3790, 1984.

Basavaiah et al., "TiCl$_4$ catalyzed tandem construction of C-C and C-O bonds: a simple and one-pot atom-economical stereoselective synthesis of spiro-oxindoles," *Chem. Commun.* 2621-2623, 2005.

Bean et al., "Lidocaine Block of Cardiac Sodium Channels," *J. Gen. Physiol.* 81: 613-642, May 1983.

Bennett and Xie, "A peripheral mononeuropathy in rat that produces disorders of pain sensation like those seen in man," *Pain* 33: 87-107, 1988.

Beyersbergen Van Henegouwen et al., "First Total Synthesis of *ent*-Gelsedine via a Novel Iodide-Promoted Allene *N*-Acyliminium Ion Cyclization," *J. Org. Chem.* 65(24): 8317-8325, 2000.

Beyersbergen Van Henegouwen et al., "Total Synthesis of (+)-Gelsedine," *Angw. Chem. Int. Ed.* 38(15): 2214-2217, 1999.

Billert and Beckert, "Beiträge zur Chemie der Pyrido[1,2-α]pyrazine—Reaktivität gegenüber Heterocumulenen der Kohlensäurereihe und Ketenen," *J. Prakt. Chem.* 341(4): 332-341, 1999.

Binder et al., "Disease mechanisms in neuropathic itch," *Nature Clinical Practice/ Neurology* 4(6): 329-337, Jun. 2008.

Blair and Bean, "Roles of Tetrodotoxin (TTX)-Sensitive Na$^+$ Current, TTX-Resistant Na$^+$ Current, and Ca$^{2+}$ Current in the Action Potentials of Nociceptive Sensory Neurons," *Journal of Neuroscience* 22(23): 10277-10290, Dec. 1, 2002.

Bond et al., "Cyclopiamines A and B, Novel Oxindole Metabolites of *Penicillium cyclopium* Westling," *Journal of the Chemical Society, Perkin Transaction 1: Organic and Bio-Organic Chemistry* 7: 1751-1761, 1979.

Brackenbury and Djamgoz, "Activity-dependent regulation of voltage-gated Na$^+$ channel expression in Mat-LyLu rat prostate cancer cell line," *J. Physiol.* 573.2: 343-356, 2006.

Bramson et al., "Oxindole-Based Inhibitors of Cyclin-Dependent Kinase 2 (CDK2): Design, Synthesis, Enzymatic Activities, and X-ray Crystallographic Analysis," *J. Med. Chem.* 44: 4339-4358, 2001.

Braude and Lindwall, "Condensations of Isatin with Acetone by the Knoevenagel Method," *Journal of the American Chemical Society* 55: 325-327, Jan. 1933.

Byrn et al., "Chapter 11, Hydrates and Solvates," in *Solid-State Chemistry of Drugs*, Second Edition, 1999, pp. 233-247.

Caldwell et al., "Sodium channel Na$_v$1.6 is localized at nodes of Ranvier, dendrites, and synapses," *PNAS* 97(10): 5616-5620, May 9, 2000.

Cañas-Rodriguez and Leeming, "N-Phenyl-2-indolinones and N-Phenylindolines. A New Class of Antidepressant Agents," *Journal of Medicinal Chemistry* 15(7): 762-770, 1972.

Capilla et al., "Synthesis of isoquinolines and tetrahydroisoquinolines as potential antitumour agents," *Tetrahedron* 57: 8297-8303, 2001.

Carlson et al., "Potential hypolipidemic agents: VI. Syntheses of some new halo-substituted pyridine compounds. Effects on noradrenaline-stimulated free fatty acid mobilization," *Acta Pharm. Suecica* 9: 411-418, 1972.

Cassebaum and Liedel, "Beziehungen zwischen Konstitution und α-Aminosäure-dehydrogenasewirkung von Isatinen," *Journal für praktische Chemie* 4(12):91-95, 1960.

Catterall, "Molecular mechanisms of gating and drug block of sodium channels," *2002 Sodium channels and neuronal hyperexcitability*, Wiley, Chichester (Novartis Foundation Symposium 241), p. 206-225.

Cestèle and Catterall, "Molecular mechanisms of neurotoxin action on voltage-gated sodium channels," *Biochimie* 82: 883-892, 2000.

Chande et al., "Facile synthesis of active antitubercular, cytotoxic and antibacterial agents: a Michael addition approach," *European journal of Medicinal Chemistry* 40: 1143-1148, 2005.

Chaplan et al., "Quantitative assessment of tactile allodynia in the rat paw," *Journal of Neuroscience Methods* 53: 55-63, 1994.

Chioni et al., "A novel adhesion molecule in human breast cancer cells: Voltage-gated Na$^+$ channel β1 subunit," *The International Journal of Biochemistry & Cell Biology* 41: 1216-1227, 2009.

Chung and Chung, "Sodium channels and neuropathic pain," *Novartis Found Symposium* 261: 19-31, 2004.

Clare et al., "Voltage-gated sodium channels as therapeutic targets," *Drug Discovery Today* 5(11): 506-520, Nov. 2000.

Claudi et al., "Synthesis and Dopamine Receptor Affinities of 2-(4-Fluoro-3-hydroxyphenyl)ethylamine and N-Substituted Derivatives," *J. Med. Chem.* 33: 2408-2412, 1990.

Coppola, "*N*-Arylation of Isatins. A Direct Route to *N*-Arylisatoic Anhydrides," *J. Heterocyclic Chem.* 24: 1249-1251, Sep./Oct. 1987.

Cossy et al., "A Convenient Route to Spiropyrrolidinyl-Oxindole Alkaloids via C-3 Substituted Ene-Pyrrolidine Carbamate Radical Cyclization," *Tetrahedron Letters* 39: 2331-2332, 1998.

Cox et al., "An *SCN9A* channelopathy causes congenital inability to experience pain," *Nature* 444: 894-898, Dec. 14, 2006.

Craner et al., "Molecular changes in neurons in multiple sclerosis: Altered axonal expression of Na$_v$1.2 and Na$_v$1.6 sodium channels and Na$^+$/Ca$^{2+}$ exchanger," *PNAS* 101(21): 8168-8173, May 25, 2004.

Cravotto et al., "Azomethine Ylide Cycloaddition/Reductive Heterocyclization Approach to Oxindole Alkaloids: Asymmetric Synthesis of (—)-Horsfiline," *J. Org. Chem.* 66(25): 8447-8453, 2001.

Creveling and Daly, "Batrachotoxinin A [$^3$H]Benzoate Binding to Sodium Channels," *Methods in Neurosciences* 8: 25-37, 1992.

Cube et al., "3-(2-Ethoxy-4- {4-[3-hydroxy-2-methyl-4-(3-methylbutanoyl)-phenoxy]butoxy}phenyl)propanoic acid: a brain penetrant allosteric potentiator at the metabotropic glutamate receptor 2 (mGluR2)," *Bioorganic & Medicinal Chemistry Letters* 15: 2389-2393, 2005.

Dallacker and Sanders, "Darstellung and Reaktionen von 5-(3'-Hydroxy-oxindol-3'-yl)-1,3-benzdioxole," *Chemiker-Zeitung* 110(11): 405-411, 1986.

Devers and Galer, "Topical Lidocaine Patch Relieves a Variety of Neuropathic Pain Conditions: An Open-Label Study," *Clinical Journal* 16(3): 205-208, Sep. 2000, obtained from URL=http://ovidsp.tx.ovid.com/spb/ovidweb.cgi, download date Apr. 18, 2008, 5 pages.

Dib-Hajj et al., "Genetics and Molecular Pathophysiology of Na$_v$1.7-Related Pain Syndromes," *Advances in Genetics* 63: 85-110, 2008.

Dib-Hajj et al., "NaN, a novel voltage-gated Na channel, is expressed preferentially in peripheral sensory neurons and down-regulated after axotomy," *Proc. Natl. Acad. Sci. USA* 95: 8963-8968, Jul. 1998.

Dierks et al., "A Method for the Simultaneous Evaluation of the Activities of Seven Major Human Drug-Metabolizing Cytochrome P450S Using an In Vitro Cocktail of Probe Substrates and Fast Gradient Liquid Chromatography Tandem Mass Spectrometry," *Drug Metabolism and Disposition* 29(1): 23-29, 2001.

Ding et al., "Structure-Based Design of Spiro-oxindoles as Potent, Specific Small-Molecule Inhibitors of the MDM2-p53 Interaction," *J. Med. Chem* 49(12): 3432-3435, 2006.

Diss et al., "A potential novel marker for human prostate cancer: voltage-gated sodium channel expression in vivo," *Prostate Cancer and Prostatic Diseases* 8: 266-273, 2005.

Diss et al., "Expression Profiles of Voltage-Gated Na$^+$ Channel α-Subunit Genes in Rat and Human Prostate Cancer Cell Lines," *The Prostate* 48:165-178, 2001.

Diss et al., "Identification and characterization of the promoter region of the Nav1.7 voltage-gated sodium channel gene (*SCN9A*)," *Mol. Cell. Neurosci.* 37: 537-547, 2008.

Do and Bean, "Subthreshold Sodium Currents and Pacemaking of Subthalamic Neurons: Modulation by Slow Inactivation," *Neuron* 39: 109-120, Jul. 3, 2003.

Domingo et al., "Studies on the Biosynthesis of Paraherquamide A and VM99955. A Theoretical Study of Intramolecular Diels—Alder Cycloaddition," *J. Org. Chem.* 68(7): 2895-2902, 2003.

Doyle et al., "Rhodium (II) Acetate and Nafion-H Catalyzed Decomposition of *N*-Aryldiazoamides. An Efficient Synthesis of 2(3*H*)-Indolinones," *J. Org. Chem* 53(5): 1017-1022, 1988.

(56) References Cited

OTHER PUBLICATIONS

Dubuisson and Dennis, "The Formalin Test: A Quantitative Study of the Analgesic Effects of Morphine, Meperidine, and Brain Stem Stimulation in Rats and Cats," *Pain* 4: 161-174, 1977.
Dutton et al., "A Total Synthesis of Gelsemine. Oxindole Spiroannelation," *J. Chem. Soc., Chem. Commun.* 765-766, 1994.
Dutton et al., "Synthesis of Hindered Spiro-Oxindoles by Photolysis of 1-(1-Alkenyl(benzotriazoles)," *Tetrahedron* 55: 11927-11942, 1999.
El-Ahl, "Three-Component 1,3-Dipolar Cycloaddition Reactions in Synthesis of Spiro[pyrrolidine-2,3'-oxindoline] Derivatives," *Heteroatom Chemistry* 13 4 : 324-329, 2002.
El-Gendy and Ahmedy, "Synthesis and Antimicrobial Activity of some New 2-Indolinone Derived Oximes and Spiro-Isoxazolines," *Arch. Pharm. Res.* 23(4): 310-314, 2000.
Ettinger and Argoff, "Use of Antiepileptic Drugs for Nonepileptic Conditions: Psychiatric Disorders and Chronic Pain," *Neurotherapeutics: The Journal of the American Society for Experimental Neuro Therapeutics* 4:75-83, Jan. 2007.
Feldman and Karatjas, "Extending Pummerer Reaction Chemistry. Asymmetric Synthesis of Spirocyclic Oxindoles via Chiral Indole-2-sulfoxides," *Org. Lett.* 8(18): 4137-4140, 2006.
Feldman et al., "Extending Pummerer Reaction Chemistry. Development of a Strategy for the Regio- and Stereoselective Oxidative Cyclization of 3-(ω-Nucleophile)-Tethered Indoles," *J. Org. Chem.* 70(16): 6429-6440, 2005.
Feldman and Vidulova, "Extending Pummerer Reaction Chemistry. Application to the Oxidative Cyclization of Indole Derivatives," *Organic Letters* 6(11): 1869-1871, 2004.
Fishman et al., "Intravenous Lidocaine for Treatment-resistant Pruritus," *American Journal of Medicine* 102: 584-585, Jun. 1997.
Flanagan et al., "Radical cyclisation reactions with indoles," *Tetrahedron Letters* 44: 1795-1798, 2003.
Fokas et al., "Solution Phase Synthesis of a Spiro[pyrrolidine-2,3'-oxindole] Library via a Three Component 1,3-Dipolar Cycloaddition Reaction," *Tetrahedron Letters* 39: 2235-2238, 1998.
Foster et al., "457. Furano-compounds. Part VII. A Synthesis of 2 : 3-Dihydropsoralene," *J. Chem. Soc.* 2254-2260, 1948.
Fraser et al., "Voltage-Gated Sodium Channel Expression and Potentiation of Human Breast Cancer Metastasis," *Clin. Cancer Res.* 11(15): 5381-5389, Aug. 1, 2005.
Fuchs and Funk, "Indol-2-one Intermediates: Mechanistic Evidence and Synthetic Utility. Total Syntheses of (±)-Flustramines A and C," *Org. Lett.* 7(4): 677-680, 2005.
Fuchs and See, "Basolateral amygdala inactivation abolishes conditioned stimulus- and heroin-induced reinstatement of extinguished heroin-seeking behavior in rats," *Psychopharmacology* 160: 425-433, 2002.
Fuji et al., "Direct Asymmetric Synthesis of Quaternary Carbon Centers via Addition-Elimination Process: Nitroolefination of α-Substituted δ-Lactones," *J. Am. Chem. Soc.* 111: 7921-7925, 1989.
Fujita et al., "The Beckmann Rearrangement by Means of Phosphoryl Chloride/N,N-Dimethylacetamide; A Novel and Convenient Method for Preparing Benzoxazoles," *Synthesis* 68-69, Jan. 1982.
Gálvez and García, "Synthesis of Isomeric β-Haloethylthienopyrroles," *J. Heterocyclic Chem.* 21: 393-395, Mar.-Apr. 1984.
Ganguly et al., "Solution- and solid-phase synthesis of enantiomerically pure spiro oxindoles," *Tetrahedron Letters* 43: 8981-8983, 2002.
Ganguly et al., "Synthesis of heterocyclic compounds using radical reactions and evidence for the formation of spiro radical intermediates," *Tetrahedron Letters* 45: 883-886, 2004. *See also* Ganguly et al., "Corrigendum to 'Synthesis of heterocyclic compounds using radical reactions and evidence for the formation of spiro radical intermediates,'" [*Tetrahedron Letters* 45: 883-886, 2004],*Tetrahedron Letters* 45: 3835, 2004.
Garden et al., "A versatile synthetic methodology for the synthesis of tryptophols," *Tetrahedron* 58: 8399-8412, 2002.
Garden et al., "Investigation of the selective reduction of isatin derivatives. Synthesis of α-hydroxyacetophenone derivatives and ethyl *spiro*-3,3-(ethylenedioxy)-2-hydroxyindoline carboxylates," *Tetrahedron Letters* 44: 7617-7621, 2003.
Goldberg et al., "Loss-of-function mutations in the $Na^v1.7$ gene underlie congenital indifference to pain in multiple human populations," *Clin. Genet.* 71: 311-319, 2007.
Goldberg, "The Significance of Molecular Type, Shape and Complementarity in Clathrate Inclusion," *Topics in Current Chemistry* 149: 1-44, 1988.
González-López De Turiso and Curran, "Radical Cyclization Approach to Spirocyclohexadienones," *Organic Letters* 7(1): 151-154, 2005.
Grigg et al., "Palladium Catalysed Ter- and Tetra-molecular Queuing Processes. One-pot Routes to 3-Spiro-2-Oxindoles and 3-Spiro-2(3H)-Benzofuranones," *Tetrahedron Letters* 37(5): 695-698, 1996.
Grigg et al., "Spiro-oxindoles via bimetallic [Pd(0)/Ag(I)] catalytic intramolecular Heck-1,3-dipolar cycloaddition cascade reactions," *Tetrahedron Letters* 43: 2605-2608, 2002.
Grigoryan et al., "Synthesis and antispasmodic activity of spiro[β-carbolineindolones] and spiro[indoleindolo[2,3-c]azepinones]," *Hayastani Kimiakan Handes* 58(3): 100-104, 2005, Caplus Database Accession No. 2005:876436, 4 pages, Abstract only.
Guillaumet et al., "Synthese d'un analogue dioxinique du psoralene," *Tetrahedron Letters* 29(22): 2665-2666, 1988.
Hains et al., "Upregulation of Sodium Channel $Na_v1.3$ and Functional Involvement in Neuronal Hyperexcitability Associated with Central Neuropathic Pain after Spinal Cord Injury," *Journal of Neuroscience* 23(26): 8881-8892, Oct. 1, 2003.
Hamann et al., "Motor disturbances in mice with deficiency of the sodium channel gene *Scn8a* show features of human dystonia," *Experimental Neurology* 184: 830-838, 2003.
Haufe et al., "The promiscuous nature of the cardiac sodium current," *Journal of Molecular and Cellular Cardiology* 42: 469-477, 2007.
Hiemstra et al., "Models of Folate Coenzymes—VIII: An Approach to Yohimbane Alkaloids Via Carbon-Fragment Transfer From $N^5$, $N^{10}$-Methylenetetrahydrofolate Models," *Tetrahedron* 39(23): 1981-1986, 1983.
Hille, "Local Anesthetics: Hydrophilic and Hydrophobic Pathways for the Drug-Receptor Reaction," *The Journal of General Physiology* 69: 497-515, 1977.
Hille, "The pH-Dependent Rate of Action of Local Anesthetics on the Node of Ranvier," *The Journal of General Physiology* 69: 475-496, 1977.
Hoffman, *Organic Chemistry: An Intermediate Text—Second Edition*, John Wiley & Sons, Inc., Hoboken, New Jersey, 2004, 124, 138-144.
Ikoma et al., "The neurobiology of itch," *Nature Reviews Neuroscience* 7: 535-547, Jul. 2006.
Ikoma et al., "Neuronal Sensitization for Histamine-Induced Itch in Lesional Skin of Patients With Atopic Dermatitis," *Arch Dermatol.* 139: 1455-1458, Nov. 2003.
Inan et al , "Inhibitory effect of lidocaine on pain and itch using formalin-induced nociception and 5'-guanidinonaltrindole-induced scratching models in mice: Behavioral and neuroanatomical evidence," *European Journal of Pharmacology* 616: 141-146, 2009.
Iranpoor et al., "A novel method for the highly efficient synthesis of 1,2-benzisoxazoles under neutral conditions using the $Ph^3P/DDQ$ system," *Tetrahedron Letters* 47: 8247-8250, 2006.
Ishiyama et al., "Synthesis of Arylboronates via the Palladium(0)-Catalyzed Cross-Coupling Reaction of Tetra(alkoxo)diborons with Aryl Triflates," *Tetrahedron Letters* 38(19): 3447-3450, 1997.
Islip and White, "236. Some Reactions of 2-(3-Oxindolyl)ethylamines," *Journal of the Chemical Society* 1201-1204, 1964.
Itoh et al., "Introduction of a Hydroxy Group at the Para Position and *N*-Iodophenylation of *N*-Arylamides Using Phenyliodine(III) Bis(Trifluoracetate)," *J. Org. Chem.* 67: 7424-7428, 2002.
Jarvis et al., "A-803467, a potent and selective $Na_v1.8$ sodium channel blocker, attenuates neuropathic and inflammatory pain in the rat," *PNAS* 104(20): 8520-8525, May 15, 2007.

(56) References Cited

OTHER PUBLICATIONS

Jorgensen and Berteau, "Thyroxine Analogs. 21. o- and m-L-Thyroxine and Related Compounds," *Journal of Medicinal Chemistry* 14(12): 1199-1202, 1971.

Julian et al., "Studies in the Indole Series. VI. On the Synthesis of Oxytryptophan and Further Studies of 3-Alkylation of Oxindoles," *Journal of the American Chemical Society* 57: 2026-2029, Nov. 1935.

Julian et al., "Studies in the Indole Series. VIII. Yohimbine (Part 1). The Mechanism of Dehydrogenation of Yohimbine and Related Compounds," *Journal of the American Chemical Society* 70: 174-179, Jan. 1948.

Kaila et al., "Synthesis and Biological Evaluation of Quinoline Salicylic Acids as P-Selectin Antagonists," *J. Med. Chem.* 50: 21-39, 2007.

Kamara et al., "The First Direct Transformation of 2,2'-Dihydroxychalcones into Coumestans," *Tetrahedron* 55: 861-868, 1999.

Kamiya et al., "A Nonsense Mutation of the Sodium Channel Gene *SCN2A* in a Patient with Intractable Epilepsy and Mental Decline," *Journal of Neuroscience* 24(11): 2690-2698, Mar. 17, 2004.

Kang et al., "Pteropodine and isopteropodine positively modulate the function of rat muscarinic $M_1$ and $5-HT_2$ receptors expressed in *Xenopus* oocyte," *European Journal of Pharmacology* 444: 39-45, 2002.

Karp et al., "Preparation of 4-Hydroxy-2-trifluoromethylthiophene: A Novel Bioisostere of α,α,α-Trifluoro-m-cresol," *Synthesis* 8: 1078-1080, 2000.

Kende et al., "Intramolecular Radical Cyclization of Phenolic Enolates," *J. Am. Chem. Soc.* 110: 2210-2218, 1988.

Kim et al., "BACE1 regulates voltage-gated sodium channels and neuronal activity," *Nature Cell Biology* 9(7): 755-764, Jul. 2007.

Kim et al., "Design, synthesis, and evaluation of dioxane-based antiviral agents targeted against the Sindbis virus capsid protein," *Bioorganic & Medicinal Chemistry Letters* 15: 3207-3211, 2005.

King et al., "Hydroxy-quinoxalines and -phenazines, and Experiments on the Preparation of Hydroxyquinoxaline Di-*N*-oxides," *J. Chem. Soc.* 3012-3016, 1949.

Kirmse et al., "Intramolecular Reactivity of Arylcarbenes: Derivatives of *o*-Tolylcarbene," *J. Org. Chem.* 59: 3821-3829, 1994.

Kis-Toth et al., "Voltage-Gated Sodium Channel Nav1.7 Maintains the Membrane Potential and Regulates the Activation and Chemokine-Induced Migration of a Monocyte-Derived Dendritic Cell Subset," *The Journal of Immunology* 187: 1273-1280, 2011.

Klugbauer et al., "Structure and functional expression of a new member of the tetrodotoxin-sensitive voltage-activated sodium channel family from human neuroendocrine cells," *EMBO J.* 14(6): 1084-1090, 1995.

Kobayashi and Furukawa, "Studies on Indole Derivatives. I. Synthesis of 3-Phenyl-9*H*-pyridazino-[3,4-*b*]indole Derivatives," *Chemical & Pharmaceutical Bulletin* 12(10): 1129-1135, Oct. 1964.

Kollmar et al., "2-Amino-3-Fluorobenzoic Acid [Benzoic acid, 2-amino-3-fluoro-]," *Organic Syntheses, Coll.* 79: 196, 2002, 5 pages.

Kornet and Thio, "Oxindole-3-spiropyrrolidines and -piperidines. Synthesis and Local Anesthetic Activity," *Journal of Medicinal Chemistry* 19(7): 892-898, 1976.

Kotha et al., "Recent applications of the Suzuki-Miyaura cross-coupling reaction in organic synthesis," *Tetrahedron* 58: 9633-9695, 2002.

Kubo et al., "Michael Additions of Indoles to 2-oxoindolin-3-ylidene Ketones," *Heterocycles* 4(10), 1675-1680, 1976.

Kumar et al., "A New Route to Spiropyrrolidinyl-oxindole Alkaloids via Iodide Ion Induced Rearrangement of [(*N*-Aziridinomethylthio)methylene]-2-oxindoles," *Organic Letters* 3(26): 4193-4196, 2001.

Kuzma et al., "Progress in the Development of Ultra-Long-Acting Local Anesthetics," *Regional Anesthesia* 22(6): 543-551, Nov.-Dec. 1997.

Lackey and Sternbach, "Synthesis of Substituted Quinoline-4-carboxylic Acids," *Synthesis*: 993-997, Oct. 1993.

Lai et al., "The role of voltage-gated sodium channels in neuropathic pain," *Current Opinion in Neurobiology* 13:291-297, 2003.

Lange et al., "Regioselective Aminomethylations of Bicyclic Phenols," *Heterocycles* 53(1): 197-204, 2000.

Laniado et al., "Short Communication: Expression and Functional Analysis of Voltage-Activated $Na^+$ Channels in Human Prostate Cancer Cell Lines and their Contribution to Invasion in Vitro," *American Journal of Pathology* 150(4): 1213-1221, Apr. 1997.

Laus et al., "Analysis of the kinetics of isomerization of spiro oxindole alkaloids," *J. Chem. Soc., Perkin Trans.* 2: 1931-1936, 1996.

Laus, "Kinetics of isomerization of tetracyclic spiro oxindole alkaloids," *J. Chem. Soc., Perkin Trans.* 2: 315-317, 1998.

Le Bourdonnec et al., "Medicinal Chemistry Strategies to Reduce CYP2D6 Inhibitory Activity of Lead Candidates," *Current Medicinal Chemistry* 16: 3093-3121, 2009.

Lee-Son et al., "Stereoselective Inhibition of Neuronal Sodium Channels by Local Anesthetics," *Anesthesiolos* 77: 324-335, 1992.

Lerchner and Carreira, "Synthesis of (±)-Strychnofoline via a Highly Convergent Selective Annulation Reaction," *Chem. Eur. J.* 12: 8208-8219, 2006.

Leuwer et al., "An improved model for the binding of lidocaine and structurally related local anaesthetics to fast-inactivated voltage-operated sodium channels, showing evidence of cooperativity," *British Journal of Pharmacology* 141(1): 47-54, 2004.

Li et al., "A case of primary erythermalgia with prurigo," *Clinical and Experimental Dermatology* 34: e313-e314, 2009.

Lindemann et al., "Zur Kenntnis der Indoxazene," *Justus Liebigs Annalen der Chemie* 456: 284-311, 1927.

Lindwall and Maclennan, "A Condensation of Acetophenone with Isatin by the Knoevenagel Method," *Journal of the American Chemical Society* 54: 4739-4744, Dec. 1932.

Liu et al., "Mutations in Cardiac Sodium Channels: Clinical Implications," *Am. J. Pharmacogenomics* 3(3): 173-179, 2003.

Lorenz et al., "Binary and ternary phase diagrams of two enantiomers in solvent systems," *Thermochimica Acta* 382: 129-142, 2002.

Lossin et al., "Molecular Basis of an Inherited Epilepsy," *Neuron* 34: 877-884, Jun. 13, 2002.

Loudon and Ogg, "2:3-Dihydro-3-oxobenz-1:4-oxazines," *J. Chem. Soc.*: 739-744, 1955.

Lutz and Clark, "Acid-Catalyzed Rearrangements of the γ-(Methylanilino)lactone of cis-β-(p-Bromobenzoyl)-β-methylacrylic Acid, and of trans-β-(p-Bromobenzoyl)acrylic Methylanilide, to Oxindoles," *J. Org. Chem.* 25: 193-196, Feb. 1960.

Lyalin et al., [title unavailable], *Zhurnal Organicheskoi Khimii* 20(4): 846-849, 1984.

Ma and Cai, "*N,N*-Dimethyl Glycine-Promoted Ullmann Coupling Reaction of Phenols and Aryl Halides," *Organic Letters* 5(21): 3799-3802, 2003.

MacNicol, "Clathrates and Molecular Inclusion Phenomena," *Chemical Society Reviews* 7(1): 65-87, 1978.

Maercker and Theysohn, "Versuche zur Umlagerung von 2-Cyclopropyl-äthyl-Anionen," *Liebigs Ann. Chem.* 759: 132-157, 1972.

Maginnity and Gaulin, "Derivatives of *o*-, *m*- and *p*-Aminobenzotrifluoride," *J. Am. Chem. Soc.* 73: 3579-3580, Aug. 1951.

Majumdar et al., "1-Alkylisatins via Aldol-Retro-aldol Condensation," *J. Chem. Research (S)*, 460-461, 1996.

Mann et al., "The Synthesis of Lignans and Related Structures using Quinodimethanes and Isobenzofurans: Approaches to the Podophyllins," *J. Chem. Soc. Perkin Trans. I*: 2081-2088, 1984.

Mannaioni et al., "Tryptophan Metabolism and Hepatic Encephalopathy. Studies on the Sedative Properties of Oxindole," *Advances in experimental medicine and biology* 467: 155-167, 1999.

Mao and Baldwin, "New Spirocyclic Oxindole Synthesis Based on a Hetero Claisen Rearrangement," *Organic Letters* 6(14): 2425-2428, 2004.

Mao and Chen, "Systemic lidocaine for neuropathic pain relief," *Pain* 87: 7-17, 2000.

(56) References Cited

OTHER PUBLICATIONS

Marcantonio et al., "An Investigation into Causes and Effects of High Cyanide Levels in the Palladium-Catalyzed Cyanation Reaction," *Organic Letters* 6(21): 3723-3725, 2004.

Marti and Carreira, "Construction of Spiro[pyrrolidine-3,3'-oxindoles]—Recent Applications to the Synthesis of Oxindole Alkaloids," *Eur. J. Org. Chem.* 2209-2219, 2003.

Marti and Carreira, "Total Synthesis of (—)-Spirotryprostatin B: Synthesis and Related Studies," *J. Am. Chem. Soc.* 127(32): 11505-11515, 2005.

McMurtrey and Daves, Jr., "König's Adducts of N-Alkyl(aryl)aminoethanols and Quinones. 3,4-Dihydro-4-alkyl(aryl)-8a-hydroxy-2H-1,4,benzoxazin-6(8aH)-ones," *J. Org. Chem.* 35(12): 4252-4253, 1970.

McNeal et al., "[$^3$H]Batrachotoxinin a 20α-Benzoate Binding to Voltage-Sensitive Sodium Channels: A Rapid and Quantitative Assay for Local Anesthetic Activity in a Variety of Drugs," *J. Med. Chem.* 28(3): 381-388, 1985.

Meisler et al., "Sodium channel gene family: epilepsy mutations, gene interactions and modifier effects," *J. Physiol.* 588.11: 1841-1848, 2010.

Miyake et al., "Preparation and Synthetic Applications of 2-Halotryptamines: Synthesis of Elacomin and Isoelacomine," *Organic Letters* 6(5): 711-713, 2004.

Miyamoto et al., "Highly Diastereoselective One-Pot Synthesis of Spirocyclic Oxindoles through Intramolecular Ullmann Coupling and Claisen Rearrangement," *Angew. Chem. Int. Ed.* 45: 2274-2277, 2006.

Miyaura and Suzuki, "Palladium-Catalyzed Cross-Coupling Reactions of Organoboron Compounds," *Chem. Rev.* 95: 2457-2483, 1995.

Morie et al., "Asymmetric Synthesis of the Enantiomers of 2-Aminomethyl-4-(4-Fluorobenzyl)morpholine, an Intermediate of Mosapride, a Gastroprokinetic Agent," *Heterocycles* 38(5): 1033-1040, 1994.

Morinville et al., "Distribution of the Voltage-Gated Sodium Channel Na$_v$1.7 in the Rat: Expression in the Autonomic and Endocrine Systems," *Journal of Comparative Neurology* 504: 680-689, 2007.

Morton et al., "Novel solid-phase synthesis of 1,5-benzothiazepine-4-one derivatives," *Tetrahedron Letters* 41: 3029-3033, 2000.

Muci and Buchwald, "Practical Palladium Catalysts for C-N. And C-O Bond Formation," *Topics in Current Chemistry* 219: 131-209, 2002.

Muhammad et al., "Two stereoisomeric pentacyclic oxindole alkaloids from Uncaria tomentosa; uncarine C and uncarine E," *Acta Cyst.* C57: 480-482, 2001.

Nagakura et al., "Allodynia and Hyperalgesia in Adjuvant-Induced Arthritic Rats: Time Course of Progression and Efficacy of Analgesics," *The Journal of Pharmacology and Experimental Therapeutics* 306(2): 490-497, 2003, obtained from URL=http://jpet.aspetjournals.org, download date Aug. 14, 2009.

Nagamura and Saito, "Antitumor Antibiotics: Duocarmycins," *Chemistry of Heterocyclic Compounds* 34(12): 1386-1405, 1998.

Nagamura et al., "Wagner-Meerwein Rearrangement of Duocarmycins," *Chem. Pharm. Bull.* 44(5): 933-939, May 1996.

Nair et al., "Formal dipolar cycloaddition of allylsilanes to o-quinonoid compounds: a convenient route to benzofused and spirofused heterocycles," *Tetrahedron Letters* 43: 5349-5351, 2002.

Nair et al., "N-Heterocyclic Carbene Catalyzed Reaction of Enals and 1,2-Dicarbonyl Compounds: Stereoselective Synthesis of Spiro γ-Butyrolactones," *Org. Lett.* 8(3): 507-509, 2006.

Nakamura et al., "Cancer preventive agents, Part 2: Synthesis and evaluation of 2-phenyl-4quinolone and 9-oxo-9,10-dihydroacridine derivatives as novel antitumor promoters," *Bioorganic & Medicinal Chemistry* 13: 4396-4401, 2005.

Namer et al., "Separate Peripheral Pathways for Pruritus in Man," *J. Neurophysiol.* 100: 2062-2069, 2008.

Newkome et al., "α-Methyl Functionalization of Electron-Poor Heterocycles: Free Radical Chlorination," *Synthesis* 676-679, Aug. 1984.

Nicolaus, *Decision Making in Drug Research*, Raven Press, New York, 1983, Franz Gross (ed.), "Symbiotic Approach to Drug Design," pp. 173-186.

Niemann et al., "The Synthesis of 3'-Fluoro-dl-thyronine and Some of its Iodinated Derivatives," *J. Am. Chem. Soc.* 63: 609-611, Feb. 1941.

Oaklander et al., "Intractable postherpetic itch and cutaneous deafferentation after facial shingles," *Pain* 96: 9-12, 2002.

Oguri et al., "Amino Acids and Peptides. XXVIII. A New Synthesis of α-Amino Acid Derivatives by Alkylation of Schiff Bases derived from Glycine and Alanine," *Chem. Pharm. Bull.* 25(9): 2287-2291, 1977.

Okita and Isobe, "Synthesis of the Pentacyclic Intermediate for Dynemicin A and Unusual Formation of Spiro-oxindole Ring," *Tetrahedron* 50(38): 11143-11152, 1994.

Onishi et al., "Concise, Asymmetric Total Synthesis of Spirotryprostatin A," *Organic Letters* 5(17): 3135-3137, 2003.

Onishi et al., "Concise, asymmetric total synthesis of spirotryprostatin A," *Tetrahedron* 60: 9503-9515, 2004.

Orlova et al., "Synthesis of 2,3,4,5-Tetrahydro-1,5-Benzox(and Thi)azepines and Their Utilization for the Preparation of Condensed Indoles," Translated from *Khimiya Geterotsiklicheskikh Soedinenii* 9: 1262-1266, Sep. 1975, 5 pages.

Overman and Watson, "Diastereoselection in the Formation of Spirocyclic Oxindoles by the Intramolecular Heck Reaction," *J. Org. Chem* 71: 2587-2599, 2006.

Papale et al., "Heterozygous mutations of the voltage-gated sodium channel SCN8A are associated with spike-wave discharges and absence epilepsy in mice," *Human Molecular Genetics* 18(9): 1633-1641, 2009.

Patani and LaVoie, "Bioisosterism: A Rational Approach in Drug Design," *Chem. Rev.* 96(8): 3147-3176, 1996.

Pearn, "Neurology of ciguatera," *J.Neurol. Neurosurg. Psychiatry* 70: 4-8, 2001.

Pereira et al., "Severe epilepsy, retardation, and dysmorphic features with a 2q deletion including SCN1A and SCN2A," *Neurology* 63: 191-192, 2004.

Pietra and Tacconi, "α-Alkyl- and α-aryl-N-methyltryptamines," *Farmaco, Edizione Scientifica* 14: 854-866, 1959, CAPLUS Database Accession No. 1960:50362, 1 page, Abstract only.

Popp and Pajouhesh, "Potential Anticonvulsants IV: Condensation of Isatin with Benzoylacetone and Isopropyl Methyl Ketone," *Journal of Pharmaceutical Sciences* 71(9): 1052-1054, Sep. 1982.

Popp et al., "Synthesis of Potential Anticonvulsants: Consensation of Isatins with Acetone and Related Ketones," *Journal of Pharmaceutical Sciences* 69(10): 1235-1237, Oct. 1980.

Popp, "Potential Anticonvulsants. V. The Condensation of Isatins with C-Acetyl Heterocyclic Compounds," *J. Heterocyclic Chem.* 19: 589-592, May-Jun. 1982.

Pouton, "Lipid formulations for oral administration of drugs: non-emulsifying, self-emulsifying and 'self-microemulsifying' drug delivery systems," *European Journal of Pharmaceutical Sciences* 11(Suppl 2): S93-S98, 2000.

Priest, "Future potential and status of selective sodium channel blockers for the treatment of pain," *Current Opinion in Drug Discovery & Development* 12(5): 682-692, 2009.

Puopolo et al., "Roles of Subthreshold Calcium Current and Sodium Current in Spontaneous Firing of Mouse Midbrain Dopamine Neurons," *Journal of Neuroscience* 27(3): 645-656, Jan. 17, 2007.

Raj and Raghunathan, "A Novel Entry into a New Class of Spiro Heterocyclic Framework: A Facile Synthesis of Dispiro[oxindole-1,2,3,4-tetrahydro-naphthalen-1-one]pyrrolidines and Spiro[1,2,3,4-tetrahydro-naphthalen-1-one]pyrrolidines," *Synthetic Communications* 33(7):1131-1139, 2003.

Raj and Raghunathan, "A novel entry into a new class of spiro-heterocyclic framework: regioselective synthesis of dispiro[oxindole-cyclohexanone]-pyrrolidines and dispiro[oxindole-hexahydroindazole]pyrrolidines," *Tetrahedron* 57: 10293-10298, 2001.

Raj et al., "Synthesis, Antimicrobial and Antifungal Activity of a New Class of Spiro Pyrrolidines,"*Bioorganic & Medicinal Chemistry* 11: 407-419, 2003.

(56) References Cited

OTHER PUBLICATIONS

Raymond et al., "Expression of Alternatively Spliced Sodium Channel α-Subunit Genes," *Journal of Biological Chemistry* 279(44): 46234-46241, Oct. 29, 2004.

Reddy et al., "Synthesis and Pharmacological Evaluation of N,N-Diarylguanidines as Potent Sodium Channel Blockers and Anticonvulsant Agents," *J. Med. Chem.* 41(17): 3298-3302, 1998.

Rehn et al., "The Three-Component Reaction between Isatin, α-Amino Acids, and Dipolarophiles," *Eur. J. Org. Chem.* 413-418, 2004.

Reimann et al., "Pain perception is altered by a nucleotide polymorphism in SCN9A," *PNAS* 107(11): 5148-5153, Mar. 16, 2010.

Ren and Dubner, "Enhanced Descending Modulation of Nociception in Rats With Persistent Hindpaw Inflamation," *Journal of Neurophysiology* 76(5): 3025-3037, Nov. 1996.

Rhodes et al., "Noninactivating voltage-gated sodium channels in severe myoclonic epilepsy of infancy," *PNAS* 101(30): 11147-11152, Jul. 27, 2004.

Rivalle and Bisagni, "Ethyl (4-N-Acylaminopyridin-3-yl)glyoxylate and 5-Azaisatin as New Synthons for a Route to Various New Polyheterocycles," *J. Heterocyclic Chem.* 34: 441-444, Mar.-Apr. 1997.

Rosevear and Wilshire, "Cyclization Reactions in Azole Chemistry: The Reaction of Some Azoles with o-Fluoro-acetophenone, o-Fluorobenzaldehyde and o-Fluorobenzophenone," *Aust. J. Chem.* 44: 1097-1114, 1991.

Ross et al., "Loss of Inhibitory Interneurons in the Dorsal Spinal Cord and Elevated Itch in Bhlhb5 Mutant Mice," *Neuron* 65: 886-898, Mar. 25, 2010.

Rossiter, "A convenient synthesis of 3-methyleneoxindoles: cytotoxic metabolites of indole-3-acetic acids," *Tetrahedron Letters* 43: 4671-4673, 2002.

Ruan et al., "Sodium channel mutations and arrhythmias," *Nature Reviews Cardiology* 6: 337-348, May 2009.

Sadler, "Separation of Isomeric Isatins," *J. Org. Chem.* 21(2): 169-170, 1956.

Saenger, "Cyclodextrin Inclusion Compounds in Research and Industry," *Angew. Chem. Int. Ed. Engl* 19: 344-362, 1980.

Sakaki et al., "Discovery of IRL 3461: A Novel and Potent Endothelin Antagonist With Balanced $ET_a/ET_b$ Affinity," *Bioorganic & Medicinal Chemistry Letters* 8: 2241-2246, 1998.

Sauviat et al., "Blockade of sodium channels by Bistramide A in voltage-clamped frog skeletal muscle fibres," *Biochimica et Biophysica Acta* 1103: 109-114, 1992.

Sawyer, "Recent Advances in Diaryl Ether Synthesis," *Tetrahedron* 56: 5045-5065, 2000.

Schmelz et al., "Specific C-Receptors for Itch in Human Skin," *The Journal of Neuroscience* 17(20): 8003-8008, Oct. 15, 1997.

Schnyder et al., "Synthesis of Primary Aromatic Amides by Aminocarbonylation of Aryl Halides Using Formamide as an Ammonia Synthon," *J. Org. Chem.* 66: 4311-4315, 2001.

Schulenburg and Archer, "An Unusual Base-catalyzed Cyclization," *Journal of the American Chemical Society* 83(14): 3091-3096, Jul. 20, 1961.

Sebahar et al., "Asymmetric, stereocontrolled total synthesis of (+) and (—)-spirotryprostatin B via a diastereoselective azomethine ylide [1,3]-dipolar cycloaddition reaction," *Tetrahedron* 58: 6311-6322, 2002.

Shin et al., "Potent inhibition of CYP2D6 by haloperidol metabolites: stereoselective inhibition by reduced haloperidol," *J. Clin. Pharmacol.* 51: 45-52, 2001.

Shoop et al., "Anthelmintic Activity of Paraherquamide in Sheep," *J. Parasitol.* 76(3): 349-351, Jun. 1990.

Simas et al., "Regioselective Lithiation of Resorcinol Derivatives: Synthesis of Mono O-MOM- and O-Benzylresorcinols Prenlated at C-2 or C-4 Positions," *Synthesis* 6: 1017-1021, 1999.

Singh et al., "Novel cAMP PDE III Inhibitors: Imidazo[4,5-b]pyridine-2(3H)-ones and Thiazolo[4,5-b]pyridin-2(3H)-ones and Their Analogs," *J. Med. Chem.* 37: 248-254, 1994.

Sircar et al., "Synthesis and SAR of N-Benzoyl-1-Biphenylalanine Dervatives: Discovery of TR-14035, A Dual $α_4β_7/α_4β_1$ Integrin Antagonist," *Bioorganic & Medicinal Chemistry Letters* 10: 2051-2066, 2002.

Smith et al., "Sodium channel protein expression enhances the invasiveness of rat and human prostate cancer cells," *FEBS Letters* 423: 19-24, 1998.

Sridhar and Raghunathan, "Rapid Access for the Synthesis of 1-N-Methyl-spiro[2.3']oxindole-spiro[3.7"]     (3"-Aryl)-5"-methyl-3",3a",4",5",6",7"-hexahydro-2H-pyrazolo[4,3-c]pyridine-4-aryl-pyrrolidines Through Sequential 1,3-Dipolar Cycloaddition and Annulation," *Synthetic Communications* 36: 21-29, 2006.

Steinhoff et al., "Proteinase-Activated Receptor-2 Mediates Itch: A Novel Pathway for Pruritus in Human Skin," *Journal of Neuroscience* 23(15): 6176-6180, Jul. 16, 2003.

Stella and Nti-Addae, "Prodrug strategies to overcome poor water solubility," *Advanced Drug Delivery Reviews* 59: 677-694, 2007.

Subramaniyan et al., "A facile entry into a new class of spiroheterocycles: synthesis of dispiro[oxindolechromanone/flavanone/tetralone]pyrroloisoquinoline ring systems," *Tetrahedron* 58: 9075-9079, 2002.

Suchý et al., "Synthesis, Absolute Configuration, and Enantiomeric Enrichment of a Cruciferous Oxindole Phytoalexin, (S)-(—)-Spirobrassinin, and Its Oxazoline Analog," *J. Org. Chem.* 66: 3940-3947, 2001.

Tacconi et al., "Heterodiene Syntheses—V 1,2-versus 1,4-cycloaddition reactions of enamines to n-substituted 3-oxindolideneacetopheones," *Tetrahedron* 27: 561-579, 1971.

Takahashi et al., "Palladium(0)-Catalyzed Carbonylation on the Multipin™ System," *Tetrahedron Letters* 40: 7843-7846, 1999.

Tamaoka, "Paramyotonia Congenita and Skeletal Sodium Channelopathy," *Internal Medicine* 42(9): 769-770, Sep. 2003.

Tanelian and Brose, "Neuropathic Pain Can Be Relieved by Drugs That Are Use-dependent Sodium Channel Blockers: Lidocaine, Carbamazepine, and Mexiletine," *Anesthesiology* 74(5): 949-951, May 1991.

Ting et al., "Substituted 1,3-Dihydro-2H-pyrrolo[2,3-b]pyridin-2-ones as Potential Antiinflammatory Agents," *J. Med. Chem.* 33(10): 2697-2706, 1990.

Tokunaga et al., "Oxindole Derivatives as Orally Active Potent Growth Hormone Secretagogues," *J. Med. Chem.* 44(26): 4641-4649, 2001.

Trost and Brennan, "Palladium Asymmetric Allylic Alkylation of Prochiral Nucleophiles: Horsfiline," *Org. Lett.* 8(10): 2027-2030, 2006.

Trost and Frederiksen, "Palladium-Catalyzed Asymmetric Allylation of Prochiral Nucleophiles: Synthesis of 3-Allyl-3-Aryl Oxindoles," *Angew. Chem. Int. Ed.* 44: 308-310, 2005.

Twycross et al., "Itch: scratching more than the surface," *Q. J. Med.* 96: 7-26, 2003.

Usman et al., "1-Acetyl-3-(2-chloro-2,3-dihydrobenzofuran-3-yl)-1,2-dihydro-3-hydroxy-2-oxo-3H-indole," *Acta Cryst.* E58: o37-o39, 2002.

Venkatesan et al., "Total Synthesis of SR 121463 A, a Highly Potent and Selective Vasopressin $V_2$ Receptor Antagonist," *Journal of Organic Chemistry* 66(11): 3653-3661, Jun. 1, 2001.

Viaud et al., "Pyrrolo[2,3-b]pyridin-2(2H)-one Derivatives as Potential Non-opioid Analgesic Agents," *Pharmaceutical Sciences* 3: 283-287, 1997.

Viaud et al., "Acylation of Oxazolo[4,5-b]pyridin-2(3H)-ones, 2-Phenyloxazolo[4,5-b]pyridines and Pyrrolo[2,3-b]pyridin-2(2H)-ones," *Tetrahedron* 53(14): 5159-5168, 1997.

Villamil et al., "Efficacy of lidocaine in the treatment of pruritus in patients with chronic cholestatic liver diseases," *The American Journal of Medicine* 118: 1160-1163, 2005.

Vippagunta et al., "Crystalline solids," *Advanced Drug Delivery Reviews* 48: 3-26, 2001.

Walker et al., "Limitations in Ring Rearrangement of Fused γ-Lactams Imposed by a Quaternary Carbon Atom. Cyclization of Acid Lactams to Spiro Keto Lactams," *J. Org. Chem.* 30(9): 2973-2983, Sep. 1965.

(56) References Cited

OTHER PUBLICATIONS

Wang and Ganesan, "A Biomimetic Total Synthesis of (—)-Spirotryprostatin B and Related Studies," *J. Org. Chem.* 65(15): 4685-4693, 2000.

Wang and Yosipovitch, "New insights into the pathophysiology and treatment of chronic itch in patients with End-stage renal disease, Chronic liver disease and Lymphoma," *Int. J. Dermatol.* 49(1): 1-11, Jan. 2010.

Watanabe et al., "$Na_v2$/NaG Channel Is Involved in Control of Salt-Intake Behavior in the CNS," *Journal of Neuroscience* 20(20): 7743-7751, Oct. 15, 2000.

Weaver et al., "Cytochrome P450 Inhibition Using Recombinant Proteins and Mass Spectrometry/Multiple Reaction Monitoring Technology in a Cassette Incubation," *Drug Metabolism and Disposition* 31(7): 955-966, 2003.

Weber and Czugler, "Functional Group Assisted Clathrate Formation'Scissor-Like and Roof-Shaped Host Molecules," *Topics in Current Chemistry* 149: 45-135, 1988.

Weidmann et al., "2-[(2-Pyridylmethyl)sulfinyl]-1$H$-thieno[3,4-$d$]imidazoles. A Novel Class of Gastric $H^+/K^+$-ATPase Inhibitors," *J. Med. Chem.* 35: 438-450, 1992.

Wolff (ed.), *Burger's Medicinal Chemistry and Drug Discovery, Fifth Edition, vol. I: Principles and Practice,* John Wiley & Sons, Inc., New York, New York, 1994, pp. 975-977.

Wood et al., "Voltage-Gated Sodium Channels and Pain Pathways," *J. Neurobiol.* 61: 55-71, 2004.

Wrona et al., "Hydroxyl Radical-Mediated Oxidation of Serotonin: Potential Insights into the Neurotoxicity of Methamphetamine," *J. Neurochem.* 64(3): 1390-1400, 1995.

Wu et al., "The Effect of Hypercholesterolemia on the Sodium Inward Currents in Cardiac Myocyte," *J. Mol. Cell. Cardiol.* 27: 1263-1269, 1995.

Xiao and Bennett, "C-fiber spontaneous discharge evoked by chronic inflammation is suppressed by a long-term infusion of lidocaine yielding nanogram per milliliter plasma levels," *Pain* 137: 218-228, 2008.

Yang and Williams, "Palladium-Catalyzed Cyanation of Aryl Bromides Promoted by Low-Level Organotin Compounds," *Organic Letters* 6(17): 2837-2840, 2004.

Yang et al., "Nucleophilic-Type Radical Cyclizations of Indoles: Conversion of 2-Cyano 3-Substituted Indoles to Spiro-Annelated Indolines and Tetrahydrocarbazolones," *J. Org. Chem.* 58: 3100-3105, 1993.

Zhang et al., "Crystal structure of *syn*-1-acetyl-9'aH-8'-methoxyspiro[indole-3,2'-oxeto[3',2':4,5]furo[3,2-g][1]benzopyran]2,6'-dione," *Journal of Chemical Crystallography* 33(3): 165-168, Mar. 2003.

Zhang et al., "Photoinduced [2+2] cycloadditions (the Paterno-Büchi reaction) of 1-acetylisatin with enol ethers—regioselectivity, diastereo-selectivity and acid catalysed transformations of the spirooxetane products," *J. Chem. Soc., Perkin Trans.* 1: 345-353, 2002.

Zhao et al., "Voltage-gated sodium channel expression in rat and human epidermal keratinocytes: Evidence for a role in pain," *Pain* 139: 90-105, 2008.

Zinser et al., "Anthelmintic paraherquamides are cholinergic antagonists in gastrointestinal nematodes and mammals," *J. vet. Pharmacol. Therap.* 25: 241-250, 2002.

Invitation to Pay Additional Fees, mailed Aug. 23, 2006, for PCTAN PCT/US2006/014845, 11 pages.

International Search Report and Written Opinion, mailed Oct. 31, 2006, for PCTAN PCT/US2006/014865, 26 pages.

International Preliminary Report on Patentability, mailed Nov. 1, 2007, for PCTAN PCT/US2006/014865, 13 pages.

Official Action from Intellectual Property India, mailed Mar. 28, 2011, for India Patent Application No. 4596/CHENP/2007, 4 pages.

Chafeev et al., Entitled Oxindole Compounds and Their Uses As Therapeutic Agents, Preliminary Amendment dated Jul. 14, 2006, for U.S. Appl. No. 11/408,269, 6 pages.

Chafeev et al., Entitled Oxindole Compounds and Their Uses As Therapeutic Agents, Restriction Requirement mailed Sep. 9, 2008, for U.S. Appl. No. 11/408,269, 10 pages.

Chafeev et al., Entitled Oxindole Compounds and Their Uses As Therapeutic Agents, Response to Restriction Requirement dated Oct. 9, 2008, for U.S. Appl. No. 11/408,269, 3 pages.

Chafeev et al., Entitled Oxindole Compounds and Their Uses As Therapeutic Agents, Office Action mailed Dec. 15, 2008, for U.S. Appl. No. 11/408,269, 29 pages.

International Search Report and Written Opinion, mailed Oct. 6, 2006, for PCTAN PCT/US2006/014352, 11 pages.

International Preliminary Report on Patentability, mailed Oct. 16, 2007, for PCTAN PCT/US2006/014352, 6 pages.

Official Action from Intellectual Property Australia, dated Jan. 12, 2011, for Patent Application No. 2006235593, 5 pages.

Response to Official Action from Intellectual Property Australia, mailed May 28, 2012, for Patent Application No. 2006235593, 60 pages.

Official Action from Canadian Intellectual Property Office, dated Aug. 14, 2012, for Patent Application No. 2,604,115, 3 pages.

Official Action from State Intellectual Property Office of China, dated Dec. 25, 2009, for Patent Application No. 200680011733.9, 4 pages.

Official Action from State Intellectual Property Office of China, dated Oct. 9, 2010, for Patent Application No. 200680011733.9, 4 pages.

Official Action from State Intellectual Property Office of China, dated Oct. 10, 2011, for Patent Application No. 201110027693.X, 5 pages.

Official Action from State Intellectual Property Office of China, dated May 9, 2012, for Patent Application No. 201110027693.X, 6 pages.

Official Action from European Patent Office, dated Apr. 9, 2010, for Patent Application No. 06 750 402.7, 4 pages.

Response to Official Action from European Patent Office, dated Aug. 19, 2010, for Patent Application No. 06 750 402.7, 105 pages.

Official Action from European Patent Office, dated Sep. 14, 2010, for Patent Application No. 06 750 402.7, 3 pages.

Response to Official Action from European Patent Office, dated Jul. 6, 2011, for Patent Application No. 06 750 402.7, 175 pages.

Official Action from European Patent Office re extended European search report, dated Feb. 2, 2012, for Patent Application No. 11009687.2, 7 pages.

Response to Official Action from European Patent Office re extended European search report, dated Dec. 13, 2012, for Patent Application No. 11009687.2, 9 pages.

Translation of Official Action from Israel Patent Office, dated Jan. 17, 2011, for Patent Application No. 186616, 3 pages.

Response to Official Action from Israel Patent Office, mailed Jul. 14, 2011, for Patent Application No. 186616, 5 pages.

Translation of Official Action from Israel Patent Office, dated Dec. 19, 2012, for Patent Application No. 186616, 3 pages.

Official Action from Intellectual Property India, mailed Apr. 29, 2011, for India Patent Application No. 4597/CHENP/2007, 2 pages.

Response to Official Action from Intellectual Property India, mailed Apr. 18, 2012, for India Patent Application No. 4597/CHENP/2007, 86 pages.

Translation of Official Action from Patent Office of Japan, mailed Nov. 22, 2011, for Patent Application No. 2008-506802, 11 pages.

Translation of Official Action from Patent Office of Japan, dated May 16, 2012, for Patent Application No. 2008-506802, 8 pages.

Official Action from Intellectual Property Office of New Zealand, dated Sep. 1, 2009, for Patent Application No. 561210, 2 pages.

Response to Official Action from Intellectual Property Office of New Zealand, dated Nov. 22, 2010, for Patent Application No. 561210, 2 pages.

Official Action from Intellectual Property Office of New Zealand, dated Nov. 30, 2010, for Patent Application No. 561210, 1 page.

Response to Official Action from Intellectual Property Office of New Zealand, dated Feb. 21, 2011, for Patent Application No. 561210, 2 pages.

Official Action from Intellectual Property Office of New Zealand, dated Feb. 25, 2011, for Patent Application No. 591268, 2 pages.

(56) References Cited

OTHER PUBLICATIONS

Official Action from Intellectual Property Office of Republic of the Philippines, dated Sep. 22, 2010, for Patent Application No. 1-2007-502050, 2 pages.
Response to Official Action from Intellectual Property Office of the Philippines, dated Jan. 20, 2011, for Patent Application No. 1-2007-502050, 85 pages.
Translation of Official Action from Intellectual Property Office of Russia, dated Mar. 16, 2010, for Patent Application No. 2007141632/04(045572), 7 pages.
Translation of Official Action from Intellectual Property Office of Russia, dated Sep. 22, 2010, for Patent Application No. 2007141632/04(045572), 7 pages.
Chafeev et al., Entitled Spiro-Oxindole Compounds and Their Uses As Therapeutic Agents, Preliminary Amendment dated Jul. 5, 2006, for U.S. Appl. No. 11/402,310, 6 pages.
Chafeev et al., Entitled Spiro-Oxindole Compounds and Their Uses As Therapeutic Agents, Restriction Requirement mailed Feb. 10, 2009, for U.S. Appl. No. 11/402,310, 7 pages.
Chafeev et al., Entitled Spiro-Oxindole Compounds and Their Uses As Therapeutic Agents, Response to Restriction Requirement dated Feb. 25, 2009, for U.S. Appl. No. 11/402,310, 109 pages.
Chafeev et al., Entitled Spiro-Oxindole Compounds and Their Uses As Therapeutic Agents, Office Action mailed May 15, 2009, for U.S. Appl. No. 11/402,310, 43 pages.
Chafeev et al., Entitled Spiro-Oxindole Compounds and Their Uses As Therapeutic Agents, Amendment dated Aug. 17, 2009, for U.S. Appl. No. 11/402,310, 150 pages.
Chafeev et al., Entitled Spiro-Oxindole Compounds and Their Uses As Therapeutic Agents, Notice of Allowance mailed Sep. 30, 2009, for U.S. Appl. No. 11/402,310, 9 pages.
Chafeev et al., Entitled Spiro-Oxindole Compounds and Their Uses As Therapeutic Agents, Statement of the Substance of the Interview, mailed Oct. 30, 2009 for U.S. Appl. No. 11/402,310, 2 pages.
Chafeev et al., Entitled Spiro-Oxindole Compounds and Their Uses As Therapeutic Agents, Communication dated Nov. 17, 2009, for U.S. Appl. No. 11/402,310, 4 pages.
Chafeev et al., Entitled Spiro-Oxindole Compounds and Their Uses As Therapeutic Agents, Office Action dated Feb. 4, 2011, for U.S. Appl. No. 12/650,196, 31 pages.
Chafeev et al., Entitled Spiro-Oxindole Compounds and Their Uses As Therapeutic Agents, Amendment and Winther Declaration dated May 4, 2011, for U.S. Appl. No. 12/650,196, 197 pages.
Chafeev et al., Entitled Spiro-Oxindole Compounds and Their Uses As Therapeutic Agents, Office Action mailed Jun. 14, 2011, for U.S. Appl. No. 12/650,196, 17 pages.
Chafeev et al., Entitled Spiro-Oxindole Compounds and Their Uses As Therapeutic Agents, Amendment dated Sep. 2, 2011, for U.S. Appl. No. 12/650,196, 15 pages.
Chafeev et al., Entitled Spiro-Oxindole Compounds and Their Uses As Therapeutic Agents, Notice of Allowance dated Sep. 20, 2011, for U.S. Appl. No. 12/650,196, 11 pages.
Sun et al., Entitled Spiro-Oxindole Compounds and Their Uses As Therapeutic Agents, Office Action dated Jul. 12, 2010, for U.S. Appl. No. 12/650,218, 26 pages.
Sun et al., Entitled Spiro-Oxindole Compounds and Their Uses As Therapeutic Agents, Amendment dated Nov. 10, 2010, for U.S. Appl. No. 12/650,218, 28 pages.
Sun et al., Entitled Spiro-Oxindole Compounds and Their Uses As Therapeutic Agents, Notice of Allowance mailed Dec. 13, 2010, for U.S. Appl. No. 12/650,218, 19 pages.
Sun et al., Entitled Spiro-Oxindole Compounds and Their Uses As Therapeutic Agents, Supplemental Amendment dated Mar. 2, 2011, for U.S. Appl. No. 12/650,218, 3 pages.
Sun et al., Entitled Spiro-Oxindole Compounds and Their Uses As Therapeutic Agents, Preliminary Amendment dated Jun. 24, 2011, for U.S. Appl. No. 13/078,678, 32 pages.
Sun et al., Entitled Spiro-Oxindole Compounds and Their Uses As Therapeutic Agents, Restriction Requirement dated Nov. 28, 2011, for U.S. Appl. No. 13/078,678, 7 pages.
Invitation to Pay Additional Fees, mailed Jan. 2, 2007, for PCTAN PCT/US2006/014887, 9 pages.
International Search Report and Written Opinion, mailed Mar. 15, 2007, for PCTAN PCT/US2006/014887, 22 pages.
International Preliminary Report on Patentability, mailed Nov. 1, 2007, for PCTAN PCT/US2006/014887, 12 pages.
Official Action from European Patent Office, dated Aug. 5, 2008, for Patent Application No. 06 758 436.7, 5 pages.
Chafeev et al., Entitled Heterocyclic Compounds and Their Uses As Therapeutic Agents, Preliminary Amendment dated Jul. 14, 2006, for U.S. Appl. No. 11/407,859, 6 pages.
Chafeev et al., Entitled Heterocyclic Compounds and Their Uses As Therapeutic Agents, Restriction Requirement mailed Mar. 31, 2008, for U.S. Appl. No. 11/407,859, 9 pages.
Chafeev et al., Entitled Heterocyclic Compounds and Their Uses As Therapeutic Agents, Response to Restriction Requirement dated Apr. 30, 2008, for U.S. Appl. No. 11/407,859, 39 pages.
Chafeev et al., Entitled Heterocyclic Compounds and Their Uses As Therapeutic Agents, Office Action mailed Jun. 20, 2008, for U.S. Appl. No. 11/407,859, 46 pages.
Chafeev et al., Entitled Heterocyclic Compounds and Their Uses As Therapeutic Agents, Amendment dated Oct. 17, 2008 for U.S. Appl. No. 11/407,859, 41 pages.
Chafeev et al., Entitled Heterocyclic Compounds and Their Uses As Therapeutic Agents, Office Action mailed Jan. 15, 2009, for U.S. Appl. No. 11/407,859, 8 pages.
International Search Report and Written Opinion, mailed Aug. 11, 2006, for PCTAN PCT/US2006/013318, 15 pages.
International Preliminary Report on Patentability, mailed Oct. 16, 2007, for PCTAN PCT/US2006/013318, 9 pages.
Official Action from European Patent Office, dated Nov. 27, 2008, for Patent Application No. 06 740 804.7, 3 pages.
Response to Official Action from European Patent Office, dated Feb. 11, 2009, for Patent Application No. 06 740 804.7, 3 pages.
Official Action from Israel Patent Office, dated Jan. 16, 2011, for Patent Application No. 186615, 3 pages.
Response to Official Action from Israel Patent Office, dated Jul. 13, 2011, for Patent Application No. 186615, 3 pages.
Official Action from Intellectual Property of India, dated May 18, 2009, for Patent Application No. 4598/CHENP/2007, 2 pages.
Response to Official Action from Intellectual Property of India, dated Mar. 15, 2010, for Patent Application No. 4598/CHENP/2007, 27 pages.
Translation of Official Action from Patent Office of Japan, dated Nov. 4, 2011, for Patent Application No. 2008-506574, 10 pages.
Official Action from Intellectual Property Corporation of Malaysia, dated May 31, 2011, for Patent Application No. PI 20061651, 3 pages.
Response to Official Action from Intellectual Property Corporation of Malaysia, filed Aug. 11, 2011, for Patent Application No. PI 20061651, 30 pages.
Official Action from Intellectual Property Office of New Zealand, dated Aug. 27, 2009, for Patent Application No. 561204, 2 pages.
Response to Official Action from Intellectual Property Office of New Zealand, dated Nov. 22, 2010, for Patent Application No. 561204, 2 pages.
Official Action from Intellectual Property Office of New Zealand, dated Dec. 6, 2010, for Patent Application No. 561204, 1 page.
Response to Official Action from Intellectual Property Office of New Zealand, dated Feb. 16, 2011, for Patent Application No. 561204, 2 pages.
Translation of Official Action from Intellectual Property Office of Russia, dated Feb. 27, 2010, for Patent Application No. 2007141633/04(045573), 4 pages.
Chafeev et al., Entitled Spiroheterocyclic Compounds and Their Uses As Therapeutic Agents, Preliminary Amendment dated Jul. 7, 2006, for U.S. Appl. No. 11/402,200, 6 pages.
Chafeev et al., Entitled Spiroheterocyclic Compounds and Their Uses As Therapeutic Agents, Restriction Requirement mailed Feb. 10, 2009, for U.S. Appl. No. 11/402,200, 6 pages.
Chafeev et al., Entitled Spiroheterocyclic Compounds and Their Uses As Therapeutic Agents, Response to Restriction Requirement dated Feb. 27, 2009, for U.S. Appl. No. 11/402,200, 31 pages.

(56) References Cited

OTHER PUBLICATIONS

Chafeev et al., Entitled Spiroheterocyclic Compounds and Their Uses As Therapeutic Agents, Office Action mailed Apr. 24, 2009, for U.S. Appl. No. 11/402,200, 30 pages.
Chafeev et al., Entitled Spiroheterocyclic Compounds and Their Uses As Therapeutic Agents, Amendment dated Aug. 24, 2009, for U.S. Appl. No. 11/402,200, 36 pages.
Chafeev et al., Entitled Spiroheterocyclic Compounds and Their Uses As Therapeutic Agents, Office Action mailed Nov. 17, 2009, for U.S. Appl. No. 11/402,200, 7 pages.
Chafeev et al., Entitled Spiroheterocyclic Compounds and Their Uses As Therapeutic Agents, Amendment dated Mar. 17, 2010, for U.S. Appl. No. 11/402,200, 17 pages.
Chafeev et al., Entitled Spiroheterocyclic Compounds and Their Uses As Therapeutic Agents, Notice of Allowance dated May 13, 2010, for U.S. Appl. No. 11/402,200, 16 pages.
Chafeev et al., Entitled Spiroheterocyclic Compounds and Their Uses As Therapeutic Agents, Preliminary Amendment dated Oct. 25, 2010, for U.S. Appl. No. 12/855,514, 32 pages.
Chafeev et al., Entitled Spiroheterocyclic Compounds and Their Uses As Therapeutic Agents, Office Action mailed Aug. 25, 2011, for U.S. Appl. No. 12/855,514, 43 pages.
International Search Report and Written Opinion, mailed Mar. 3, 2008, for PCTAN PCT/US2007/081240,16 pages.
International Preliminary Report on Patentability mailed Apr. 23, 2009, for PCTAN PCT/US2007/081240, 9 pages.
Chafeev et al., Entitled Tricyclic Spiro-Oxindole Derivatives and Their Uses As Therapeutic Agents, Restriction Requirement mailed Jan. 26, 2012, for U.S. Appl. No. 12/445,271, 7 pages.
International Search Report and Written Opinion, mailed Oct. 13, 2008, for PCTAN PCT/US2007/081323, 21 pages.
International Preliminary Report on Patentability, mailed Apr. 15, 2009, for PCTAN PCT/US2007/081323, 12 pages.
International Search Report and Written Opinion, mailed Mar. 3, 2008, for PCTAN PCT/US2007/081244, 21 pages.
International Preliminary Report on Patentability, mailed Apr. 23, 2009, for PCTAN PCT/US2007/081244, 12 pages.
Official Action from State Intellectual Property Office of China, dated May 5, 2011, for Patent Application No. 200780038272.9, 9 pages.
Official Action from State Intellectual Property Office of China, dated Feb. 20, 2012, for Patent Application No. 200780038272.9, 5 pages.
Cadieux et al., entitled Spiro (Furo [3, 2-C] Pyridine-3-3'—Indol) -2' (1'H)-One Derivatives and Related Compounds for the Treatment of Sodium-Channel Mediated Diseases, Such As Pain, Restriction Requirement mailed Apr. 19, 2012, for U.S. Appl. No. 12/445,270, 6 pages.
International Search Report and Written Opinion, mailed Apr. 1, 2011, for PCTAN PCT/US2010/052704, 12 pages.
International Preliminary Report on Patentability, mailed Apr. 17, 2012, for PCTAN PCT/US2010/052704, 6 pages.
Response to Official Action from European Patent Office, dated Dec. 14, 2012, for Patent Application No. 10 771 606.0, 25 pages.
Official Action from New Zealand Intellectual Property Office, dated Dec. 6, 2012, for Patent Application No. 599334, 2 pages.
Cadieux et al., Entitled Synthetic Methods for Spiro-Oxindole Compounds, Restriction Requirement mailed May 7, 2012, for U.S. Appl. No. 12/904,880, 7 pages.
Cadieux et al., Entitled Synthetic Methods for Spiro-Oxindole Compounds, Response to Restriction Requirement mailed Jun. 7 2012, for U.S. Appl. No. 12/904,880, 1 page.
Cadieux et al., Entitled Synthetic Methods for Spiro-Oxindole Compounds, Office Action mailed Aug. 16, 2012, for U.S. Appl. No. 12/904,880, 40 pages.
Cadieux et al., Entitled Synthetic Methods for Spiro-Oxindole Compounds, Amendment mailed Nov. 16, 2012, for U.S. Appl. NO. 12/904,880, 15 pages.
Invitation to Pay Additional Fees, mailed Jul. 16, 2008, for PCTAN PCT/US2007/081319, 10 pages.

International Search Report and Written Opinion, mailed Dec. 29, 2008, for PCTAN PCT/US2007/081319, 18 pages.
International Preliminary Report on Patentability, mailed Apr. 15, 2009, for PCTAN PCT/US2007/081319, 8 pages.
International Search Report and Written Opinion, mailed May 19, 2008, for PCTAN PCT/US2007/081247, 18 pages.
International Preliminary Report on Patentability, mailed Apr. 15, 2009, for PCTAN PCT/US2007/081247, 10 pages.
Official Action from Intellectual Property Australia, dated Mar. 22, 2012, for Patent Application No. 2007319580, 2 pages.
Translation of Official Action from State Intellectual Property Office of China, dated Oct. 28, 2010, for Patent Application No. 200780038111.X, 5 pages.
Official Action from State Intellectual Property Office of China, dated Jul. 14, 2011, for Patent Application No. 200780038111.X, 5 pages.
Official Action from State Intellectual Property Office of China, dated Jun. 8, 2012, for Patent Application No. 200780038111.X, 7 pages.
Official Action from European Patent Office, dated Jul. 7, 2009, for Patent Application No. 07 868 434.7, 3 pages.
Official Action from European Patent Office, dated Jul. 23, 2010, for Patent Application No. 07 868 434.7, 6 pages.
Response to Official Action from European Patent Office, dated May 23, 1022, for Patent Application No. 07 868 434.7, 3 pages.
Translation of Official Action from Patent Office of Japan, dated Sep. 26, 2012, for Patent Application No. 2009-532606, 5 pages.
Translation of Official Action from Intellectual Property Office of Russia, dated Aug. 31, 2011 , for Patent Application No. 2009117642, 4 pages.
Translation of Official Action from Intellectual Property Office of Russia, dated Feb. 2, 2012, for Patent Application No. 2009117642, 8 pages.
Chafeev et al., Entitled Use of Spiro-Oxindole Compounds As Therapeutic Agents, Preliminary Amendment dated Mar. 4, 2010, for U.S. Appl. No. 12/445,264, 18 pages.
Chafeev et al., Entitled Use of Spiro-Oxindole Compounds As Therapeutic Agents, Restriction Requirement mailed Aug. 24, 2012, for U.S. Appl. No. 12/445,264, 8 pages.
Chafeev et al., Entitled Use of Spiro-Oxindole Compounds As Therapeutic Agents, Response to Restriction Requirement filed Sep. 24, 2012, for U.S. Appl. No. 12/445,264, 19 pages.
International Search Report and Written Opinion, mailed May 13, 2008, for PCTAN PCT/US2007/081318, 12 pages.
International Preliminary Report on Patentability, mailed Apr. 15, 2009, for PCTAN PCT/US2007/081318, 5 pages.
International Search Report and Written Opinion, mailed Mar. 6, 2008, for PCTAN PCT/US2007/081297, 18 pages.
International Preliminary Report on Patentability, mailed Apr. 15, 2009, for PCTAN PCT/US2007/081297, 10 pages.
Invitation to Pay Additional Fees, mailed Jan. 27, 2009, for PCTAN PCT/US2007/081320, 7 pages.
Written Opinion of the International Searching Authority, mailed Jan. 5, 2009, for PCTAN PCT/US2007/081320, 11 pages.
International Preliminary Report on Patentability, mailed May 5, 2009, for PCTAN PCT/US2007/081320, 12 pages.
International Search Report and Written Opinion, mailed Dec. 1, 2011, for PCTAN PCT/US2010/052703, 13 pages.
International Preliminary Report on Patentability, mailed Apr. 17, 2012, for PCTAN PCT/US2010/052703, 9 pages.
Winters et al., Entitled Pharmaceutical Compositions for Oral Administration, Preliminary Amendment dated Dec. 27, 2010, for U.S. Appl. No. 12/905,048, 9 pages.
Winters et al., Entitled Pharmaceutical Compositions for Oral Administration, Restriction Requirement, mailed May 7, 2012, for U.S. Appl. No. 12/905,048, 9 pages.
International Search Report and Written Opinion, mailed Feb. 9, 2010, for PCTAN PCT/US2009/063290, 13 pages.
International Preliminary Report on Patentability, mailed May 10, 2011, for PCTAN PCT/US2009/063290, 7 pages.
International Search Report and Written Opinion, mailed Oct. 1, 2010, for PCTAN PCT/US2010/040187, 13 pages.

(56) References Cited

OTHER PUBLICATIONS

International Preliminary Report on Patentability, mailed Jan. 4, 2012, for PCTAN PCT/US2010/040187, 7 pages.
Response to Official Action from European Patent Office, dated Aug. 7, 2012, for Patent Application No. 10 731 662.2, 21 pages.
Response to Official Action from Philippines Intellectual Property Office, dated Jun. 15, 2012, for Patent Application No. 1-2011-502619, 3 pages.
Chafeev et al., Entitled Enantiomers of Spiro-Oxindole Compounds and Their Uses As Therapeutic Agents, Restriction Requirement mailed Jun. 20, 2011, for U.S. Appl. No. 12/825,168, 8 pages.
Chafeev et al., Entitled Enantiomers of Spiro-Oxindole Compounds and Their Uses As Therapeutic Agents, Response to Restriction Requirement and Preliminary Amendment, filed Jul. 20, 2011, for U.S. Appl. No. 12/825,168, 5 pages.
Chafeev et al. Entitled Enantiomers of Spiro-Oxindole Compounds and Their Uses As Therapeutic Agents, Office Action, mailed Aug. 29, 2011, for U.S. Appl. No. 12/825,168, 43 pages.
Chafeev et al., Entitled Enantiomers of Spiro-Oxindole Compounds and Their Uses As Therapeutic Agents, Amendment filed Jan. 30, 2012, for U.S. Appl. No. 12/825,168, 8 pages.
Chafeev et al., Entitled Enantiomers of Spiro-Oxindole Compounds and Their Uses As Therapeutic Agents, Office Action, mailed Feb. 28, 2012, for U.S. Appl. No. 12/825,168, 13 pages.
Chafeev et al., Entitled Enantiomers of Spiro-Oxindole Compounds and Their Uses As Therapeutic Agents, Amendment and Cadieux Declaration filed May 29, 2012, for U.S. Appl. No. 12/825,168, 17 pages.
Chafeev et al., Entitled Enantiomers of Spiro-Oxindole Compounds and Their Uses As Therapeutic Agents, Preliminary Amendment filed Dec. 3, 2012, for U.S. Appl. No. 13/619,915, 7 pages.
Invitation to Pay Additional Fees, mailed Feb. 9, 2010, for PCTAN PCT/US2009/060537, 8 pages.
International Search Report and Written Opinion, mailed Oct. 6, 2010, for PCTAN PCT/US2009/060537, 18 pages.
International Preliminary Report on Patentability, mailed Apr. 19, 2011, for PCTAN PCT/US2009/060537, 11 pages.
Response to Official Action from European Patent Office, dated Jan. 10, 2012, for Patent Application No. 09 740 589.8, 4 pages.
Official Action from European Patent Office, dated Sep. 11, 2012, for Patent Application No. 09 740 589.8, 5 pages.
Translation of Official Action from Korean Intellectual Property Office, dated Nov. 9, 2012, for Patent Application No. 10-2011-7011106, 9 pages.
Official Action from Intellectual Property Office of New Zealand, mailed Sep. 9, 2011, for New Zealand Patent Application No. 592275, 2 pages.
Chafeev et al., Entitled Spiro-Oxindole Compounds and Their Use As Therapeutic Agents, Preliminary Amendment dated Jan. 12, 2010, for U.S. Appl. No. 12/578,148, 57 pages.
Chafeev et al., Entitled Spiro-Oxindole Compounds and Their Use As Therapeutic Agents, Restriction Requirement mailed Aug. 15, 2011, for U.S. Appl. No. 12/578,148, 10 pages.
Chafeev et al., Entitled Spiro-Oxindole Compounds and Their Use As Therapeutic Agents, Response to Restriction Requirement dated Sep. 14, 2011, for U.S. Appl. No. 12/578,148, 57 pages.
Chafeev et al., Entitled Spiro-Oxindole Compounds and Their Use As Therapeutic Agents, Office Action mailed Oct. 21, 2011, for U.S. Appl. No. 12/578,148, 51 pages.
Chafeev et al., Entitled Spiro-Oxindole Compounds and Their Use As Therapeutic Agents, Response to Office Action dated Feb. 21, 2012, for U.S. Appl. No. 12/578,148, 46 pages.
Chafeev et al., Entitled Spiro-Oxindole Compounds and Their Use As Therapeutic Agents, Notice of Allowance dated Apr. 27, 2012 for U.S. Appl. No. 12/578,148, 12 pages.
Chafeev et al., Entitled Spiro-Oxindole Compounds and Their Use As Therapeutic Agents, Restriction Requirement mailed Oct. 10, 2012, for U.S. Appl. No. 13/557,833, 9 pages.
Chafeev et al., Entitled Spiro-Oxindole Compounds and Their Use As Therapeutic Agents, Response to Restriction Requirement filed Nov. 9, 2012, for U.S. Appl. No. 13/557,833, 14 pages.
Chafeev et al., Entitled Spiro-Oxindole Compounds and Their Use As Therapeutic Agents, Notice of Allowance mailed Nov. 27, 2012, for U.S. Appl. No. 13/557,833, 46 pages.
International Search Report and Written Opinion, mailed Jan. 22, 2010, for PCTAN PCT/US2009/060455, 14 pages.
International Preliminary Report on Patentability, mailed Apr. 19, 2011, for PCTAN PCT/US2009/060455, 7 pages.
Response to Official Action from European Patent Office, dated Feb. 1, 2012, for Patent Application No. 09 741 118.5, 12 pages.
Chafeev et al., Entitled Spiro-Oxindole Compounds and Their Use As Therapeutic Agents, Office Action dated Apr. 1, 2011, for U.S. Appl. No. 12/577,799, 49 pages.
Chafeev et al., Entitled Spiro-Oxindole Compounds and Their Use As Therapeutic Agents, Amendment dated Jul. 1, 2011, for U.S. Appl. No. 12/577,799, 21 pages.
Chafeev et al., Entitled Spiro-Oxindole Compounds and Their Use As Therapeutic Agents, Notice of Allowance mailed Oct. 7, 2011, for U.S. Appl. No. 12/577,799, 14 pages.
International Search Report and Written Opinion, mailed Apr. 8, 2010, for PCTAN PCT/US2009/069663, 13 pages.
International Preliminary Report on Patentability, mailed Jun. 29, 2011, for PCTAN PCT/US2009/069663, 6 pages.
Invitation to Pay Additional Fees, mailed Aug. 18, 2010, for PCTAN PCT/US2010/034223, 7 pages.
International Search Report and Written Opinion, mailed Jul. 11, 2011, for PCTAN PCT/US2010/034223, 18 pages.
International Preliminary Report on Patentability, mailed Nov. 15, 2011, for PCTAN PCT/US2010/034223, 11 pages.
International Search Report and Written Opinion, mailed Jun. 9, 2011, for PCTAN PCT/US2011/026359, 14 pages.
International Preliminary Report on Patentability, mailed Nov. 1, 2012, for PCTAN PCT/US2011/026359, 10 pages.
Winters et al., entitled Pharmaceutical Compositions of Spirooxindole Compound for Topical Administration and Their Use As Therapeutic Agents, Preliminary Amendment dated Oct. 30, 2012, for U.S. Appl. No. 13/580,129, 7 pages.
Official Action from European Patent Office, dated Jan. 28, 2013, for Patent Application No. 11009687.2, 3 pages.
Translation of Official Action from Korean Intellectual Property Office, mailed Feb. 27, 2013, for Patent Application No. 10-2007-7026134, 4 pages.
Cadieux et al., entitled Synthetic Methods for Spiro-Oxindole Compounds, Notice of Allowance mailed Jan. 24, 2013, for U.S. Appl. No. 12/904,880, 11 pages.
Translation of Official Action from State Intellectual Property Office of China, dated Jan. 28, 2013, for Patent Application No. 200780038111.X, 8 pages.
Chafeev et al., entitled Use of Spiro-Oxindole Compounds As Therapeutic Agents, Notice of Allowance, mailed Feb. 28, 2013, for U.S. Appl. No. 12/445,264, 56 pages.
Chafeev et al., entitled Enantiomers of Spiro-Oxindole Compounds and Their Uses As Therapeutic Agents, Notice of Allowance, mailed Jan. 31, 2013, for U.S. Appl. No. 12/825,168, 9 pages.
Chafeev et al., entitled Enantiomers of Spiro-Oxindole Compounds and Their Uses As Therapeutic Agents, Restriction Requirement mailed Feb. 27, 2013, for U.S. Appl. No. 13/619,915, 8 pages.
Translation of Official Action from State Intellectual Property Office of China, dated Mar. 29, 2013, for Patent Application No. 200980150848.X, 6 pages.
Official Action from European Patent Office, dated Feb. 19, 2013, for Patent Application No. 09 741 118.5, 5 pages.
Corey and Noe, "Preparation of *O*-Allyl-*N*-(9-Anthracenylmethyl)Cinchonidinium Bromide as a Phase Transfer Catalyst for the Enantioselective Alkylation of Glycine Benzophenone Imine *tert*-Butyl Ester: (4*S*)-2-(Benzhydrylidenamino)Pentanedioic Acid, 1-*tert*-Butyl Ester-5-Methyl Ester [[Cinchonanium, 1-(9-anthracenylmethyl)-9-(2-propenyloxy)-, bromide, (8α,9*R*)-and L-Glutamic acid, *N*-(diphenylmethylene)-, 1-(1,1-dimethylethyl) 5-methyl ester]]," *Organic Syntheses* 80(11): 38-45, 2003; Col. vol. 11: 404-409.

(56) References Cited

OTHER PUBLICATIONS

Dehmlow et al., "Monodeazacinchona Alkaloid Derivatives: Synthesis and Preliminary Applications as Phase-Transfer Catalysts," *Eur. J. Org. Chem.* 13: 2087-2093, 2002.

Li et al., "Emerging drug targets for pain treatment," *European Journal of Pharmacology* 681: 1-5, 2012.

001 and Maruoka, "Recent Advances in Asymmetric Phase-Transfer Catalysis," *Angew. Chem. Int. Ed.* 46: 4222-4266, 2007.

Swamy et al., "Mitsunobu and Related Reactions: Advances and Applications," *Chem. Rev.* 109: 2551-2651, 2009.

Response to Official Action from Canadian Intellectual Property Office, mailed Feb. 14, 2013, for Patent Application No. 2,604,115, 3 pages.

U.S. Appl. No. 13/909,964, filed Jun. 4, 2013, Chafeev et al.

Official Action from Canadian Intellectual Property Office, dated May 6, 2013, for Patent Application No. 2,604,115, 2 pages.

Official Action from State Intellectual Property Office of China, dated May 24, 2013, for Patent Application No. 201110027693.X, 12 pages.

Response to Official Action from European Patent Office, dated Jul. 18, 2013, for Patent Application No. 11009687.2, 5 pages.

Translation of Official Action from Korean Intellectual Property Office, mailed Oct. 11, 2013, for Patent Application No. 10-2013-7016857, 1 page.

Translation of Official Action from Patent Office of Japan, dated May 29, 2013, for Patent Application No. 2009-532606, 5 pages.

Translation of Official Action from State Intellectual Property Office of China, dated Jul. 17, 2013, for Patent Application No. 201080029572.2, 5 pages.

Official Action from Intellectual Property Office of New Zealand, dated Oct. 12, 2012, for Patent Application No. 596903, 1 page.

Chafeev et al., entitled Enantiomers of Spiro-Oxindole Compounds and Their Uses As Therapeutic Agents, Response to Restriction Requirement dated Jun. 27, 2013, for U.S. Appl. No. 13/619,915, 3 pages.

Chafeev et al., entitled Enantiomers of Spiro-Oxindole Compounds and Their Uses As Therapeutic Agents, Office Action mailed Sep. 30, 2013, for U.S. Appl. No. 13/619,915, 15 pages.

Official Action from Intellectual Property Australia, dated Sep. 17, 2013, for Patent Application No. 2009303468, 4 pages.

Chafeev et al., entitled Spiro-Oxindole Compounds and Their Use As Therapeutic Agents, Preliminary Amendment dated Jun. 12, 2013, for U.S. Appl. No. 13/787,558, 11 pages.

Chafeev et al., entitled Spiro-Oxindole Compounds and Their Use As Therapeutic Agents, Office Action mailed Aug. 21, 2013, for U.S. Appl. No. 13/787,558, 56 pages.

Response to Official Action from European Patent Office, dated May 23, 2013, for Patent Application No. 09 741 118.5, 65 pages.

Cadieux et al., entitled Spiro-Oxindole-Derivatives As Sodium Channel Blockers, Restriction Requirement mailed Jul. 5, 2013, for U.S. Appl. No. 13/142,375, 9 pages.

Cadieux et al., entitled Spiro-Oxindole-Derivatives As Sodium Channel Blockers, Response to Restriction Requirement filed Jul. 31, 2013, for U.S. Appl. No. 13/142,375, 2 pages.

Cadieux et al., entitled Spiro-Oxindole-Derivatives As Sodium Channel Blockers, Office Action mailed Aug. 9, 2013, for U.S. Appl. No. 13/142,375, 51 pages.

Official Action from State Intellectual Property Office of China, dated Sep. 18, 2013, for Patent Application No. 201180010245.7, 7 pages.

Official Action from European Patent Office, dated Jul. 19, 2013, for Patent Application No. 11 707 750.3, 7 pages.

Official Action from Intellectual Property Office of New Zealand, mailed May 7, 2013, for New Zealand Patent Application No. 601667, 2 pages.

Invitation to Pay Additional Fees, mailed May 3, 2013, for PCTAN PCT/US2013/030219, 5 pages.

International Search Report and Written Opinion, mailed Jun. 28, 2013, for PCTAN PCT/US2013/030219, 17 pages.

Translation of Official Action from State Intellectual Property Office of China, dated Dec. 9, 2013, for Patent Application No. 200980150848.X, 6 pages.

Official Action from European Patent Office, dated Nov. 4, 2013, for Patent Application No. 09 741 118.5, 5 pages.

\* cited by examiner

SYNTHETIC METHODS FOR SPIRO-OXINDOLE COMPOUNDS

CROSS-REFERENCE TO RELATED APPLICATIONS

This application is a divisional application of U.S. patent application Ser. No. 12/904,880, filed Oct. 14, 2010, which claims the benefit under 35 U.S.C. §119(e) of U.S. Provisional Patent Application No. 61/251,335, filed Oct. 14, 2009. These applications are incorporated herein by reference in their entirety.

FIELD OF THE INVENTION

The present invention is directed to improved methods of preparing certain spiro-oxindole compounds as well as various intermediates involved therein. In particular, this invention is directed to methods of preparing spiro-oxindole compounds, and their pharmaceutically acceptable salts, which are useful in treating sodium channel-mediated diseases or conditions, such as pain, as well as other diseases and conditions associated with the mediation of sodium channels.

BACKGROUND OF THE INVENTION

Sodium channels play a diverse set of roles in maintaining normal and pathological states, including the long recognized role that voltage gated sodium channels play in the generation of abnormal neuronal activity and neuropathic or pathological pain. Damage to peripheral nerves following trauma or disease can result in changes to sodium channel activity and the development of abnormal afferent activity including ectopic discharges from axotomised afferents and spontaneous activity of sensitized intact nociceptors. These changes can produce long-lasting abnormal hypersensitivity to normally innocuous stimuli, or allodynia. Examples of neuropathic pain include, but are not limited to, post-herpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias.

There have been some advances in treating neuropathic pain symptoms by using medications, such as gabapentin, and more recently pregabalin, as short-term, first-line treatments. However, pharmacotherapy for neuropathic pain has generally had limited success with little response to commonly used pain reducing drugs, such as NSAIDS and opiates. Consequently, there is still a considerable need to explore novel treatment modalities.

There remain a limited number of potent effective sodium channel blockers with a minimum of adverse events in the clinic. There is also an unmet medical need to treat neuropathic pain and other sodium channel associated pathological states effectively and without adverse side effects.

PCT Published Patent Application No. WO 2006/110917, PCT Published Patent Application No. WO 2010/45251 and PCT Patent Application No. PCT/US2010/040187 discloses certain spiro-oxindole compounds. These compounds are disclosed therein as being useful for the treatment of sodium channel-mediated diseases, preferably diseases related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome; neuroprotection against stroke, neural trauma and multiple sclerosis; and channelopathies such as erythromelalgia and familial rectal pain syndrome.

Methods of preparing these compounds and pharmaceutical compositions containing them are also disclosed in PCT Published Patent Application No. WO 2006/110917, PCT Published Patent Application No. WO 2010/45251 and PCT Patent Application No. PCT/US2010/040187.

There exists, therefore, a need for improved methods of preparing certain spiro-oxindole compounds.

SUMMARY OF THE INVENTION

The present invention is directed to methods of preparing certain spiro-oxindole compounds as single stereoisomers or single enantiomers, or mixtures thereof, or as pharmaceutically acceptable salts thereof. These compounds are useful in treating sodium channel-mediated diseases and conditions, such as pain.

Accordingly, in one aspect, this invention is directed to a method of preparing a compound of formula (I):

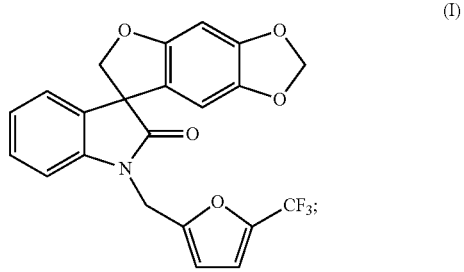 [SMILES: O=C1N(Cc2ccc(C(F)(F)F)o2)c2ccccc2C12COc1cc3c(cc12)OCO3]

or a pharmaceutically acceptable salt thereof, as a single stereoisomer or enantiomer or a mixture thereof;
wherein the method comprises treating a compound of formula (8):

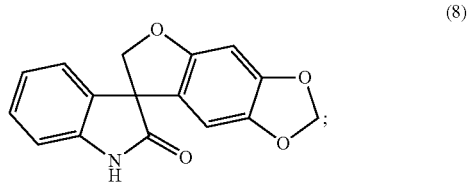 [SMILES: O=C1Nc2ccccc2C12COc1cc3c(cc12)OCO3]

or a pharmaceutically acceptable salt thereof, with a compound of formula (9):

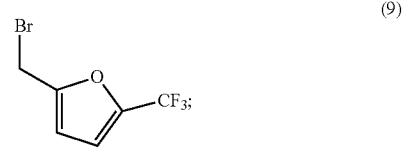 [SMILES: FC(F)(F)c1ccc(CBr)o1]

or a pharmaceutically acceptable salt thereof, under suitable conditions to provide the compound of formula (I), or a pharmaceutically acceptable salt thereof, as a single stereoisomer or enantiomer or a mixture thereof.

In another aspect, this invention is directed to a method of preparing a compound of formula (I-S):

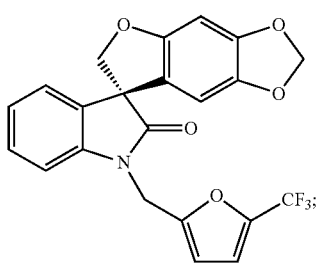

or a pharmaceutically acceptable salt thereof, and a compound of formula (I-R):

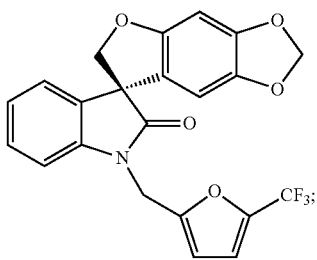

or a pharmaceutically acceptable salt thereof, wherein the method comprises resolving a compound of formula (I):

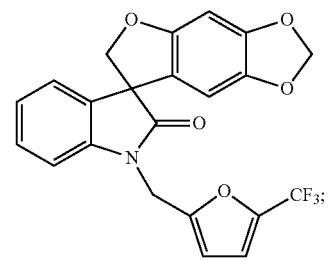

or a pharmaceutically acceptable salt thereof, as a single stereoisomer or enantiomer or a mixture thereof; under suitable conditions to yield a compound of formula (I-S), or a pharmaceutically acceptable salt thereof, and a compound of formula (I-R), or a pharmaceutically acceptable salt thereof.

In another aspect, this invention is directed to a method of preparing a compound of formula (II):

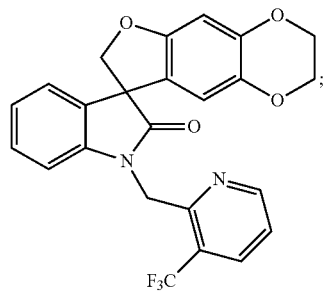

or a pharmaceutically acceptable salt thereof, as a single stereoisomer or enantiomer or a mixture thereof;
wherein the method comprises treating a compound of formula (15):

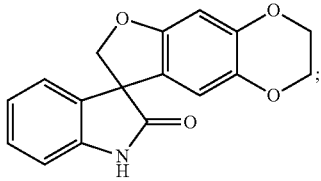

or a pharmaceutically acceptable salt thereof, with a compound of formula (16):

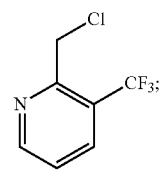

or a pharmaceutically acceptable salt thereof, under suitable conditions to provide the compound of formula (II), or a pharmaceutically acceptable salt thereof, as a single stereoisomer or enantiomer or a mixture thereof.

In another aspect, this invention is directed to a method of preparing a compound of formula (II-S):

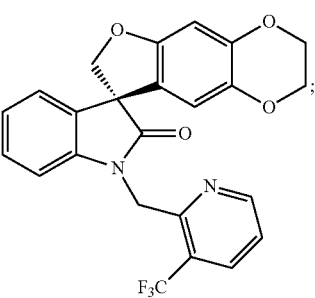

or a pharmaceutically acceptable salt thereof, and a compound of formula (II-R):

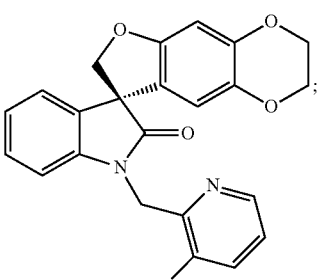

or a pharmaceutically acceptable salt thereof, wherein the method comprises resolving a compound of formula (II):

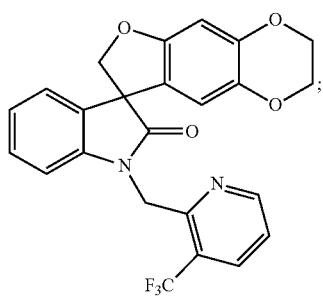

(II)

or a pharmaceutically acceptable salt thereof, as a single stereoisomer or enantiomer or a mixture thereof; under suitable conditions to yield a compound of formula (II-S), or a pharmaceutically acceptable salt thereof, and a compound of formula (II-R), or a pharmaceutically acceptable salt thereof.

DETAILED DESCRIPTION OF THE INVENTION

Definitions

As used in the specification and appended claims, unless specified to the contrary, the following terms have the meaning indicated:

"Amino" refers to the —$NH_2$ substituent.

"Cyano" refers to the —CN substituent.

"Hydroxyl" refers to the —OH substituent.

"Imino" refers to the =NH substituent.

"Nitro" refers to the —$NO_2$ substituent.

"Oxo" refers to the =O substituent.

"Trifluoromethyl" refers to the —$CF_3$ substituent.

"Analgesia" refers to an absence of pain in response to a stimulus that would normally be painful.

"Allodynia" refers to a condition in which a normally innocuous sensation, such as pressure or light touch, is perceived as being extremely painful.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, and rabbits), and non-domestic animals such as wildelife and the like.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds prepared herein may contain one or more asymmetric centres and may thus give rise to enantiomers that may be defined, in terms of absolute stereochemistry, as (R)- or (S)- or, as (D)- or (L)- for amino acids. The present invention is meant to include all such possible enantiomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation, or by the techniques disclosed herein. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

The chemical naming protocol and structure diagrams used herein are a modified form of the I.U.P.A.C. nomenclature system, using the ACD/Name Version 9.07 software program, wherein the compounds of the invention are named herein as derivatives of the central core structure, i.e., the 2-oxindole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Thus, for example, a compound of formula (I):

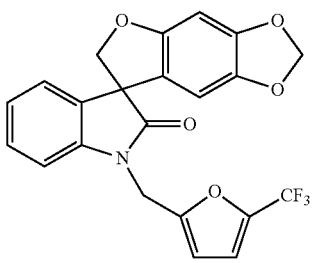

(I)

is named herein as 1-{[5-(trifluoromethyl)-2-furyl]methyl}spiro[furo[2,3-f][1,3]benzodioxole-7,3'-indol]-2'(1'H)-one.

EMBODIMENTS OF THE INVENTION

Of the various aspects of the invention set forth above in the Summary of the Invention, certain embodiments of the methods disclosed herein are preferred.

Of the method of preparing a compound of formula (I), as set forth above in the Summary of the Invention, or a pharmaceutically acceptable salt thereof, as a single stereoisomer or enantiomer or a mixture thereof, one embodiment is the method which further comprises the preparation of a compound of formula (8), or a pharmaceutically acceptable salt thereof, wherein a compound of formula (7):

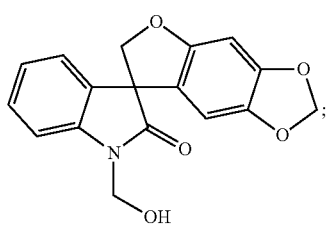

(7)

or a pharmaceutically acceptable salt thereof, is treated with a base under suitable conditions to form the compound of formula (8), or a pharmaceutically acceptable salt thereof.

Of this embodiment, another embodiment is a method which further comprises the preparation of the compound of formula (7), or a pharmaceutically acceptable salt thereof, wherein a compound of formula (6):

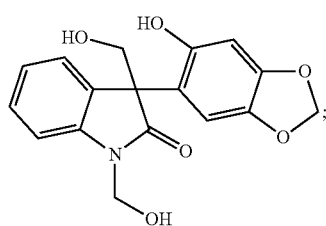

(6)

or a pharmaceutically acceptable salt thereof, is treated under standard Mitsunobu reaction conditions to form a compound of formula (5), or a pharmaceutically acceptable salt thereof.

Of this embodiment, another embodiment is a method which further comprises the preparation of the compound of formula (6), or a pharmaceutically acceptable salt thereof, wherein a compound of formula (5):

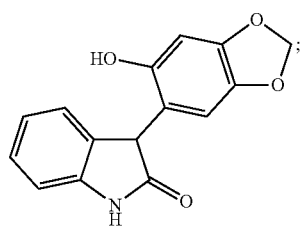

(5)

or a pharmaceutically acceptable salt thereof, is treated with an aldehyde under suitable conditions to form the compound of formula (6), or a pharmaceutically acceptable salt thereof.

Of this embodiment, another embodiment is a method which further comprises the preparation of the compound of formula (5), or a pharmaceutically acceptable salt thereof, wherein a compound of formula (4):

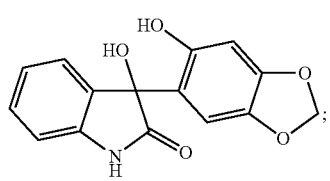

(4)

or a pharmaceutically acceptable salt thereof, is treated under suitable conditions to form the compound of formula (5), or a pharmaceutically acceptable salt thereof.

Of this embodiment, another embodiment is a method which further comprises the preparation of the compound of formula (4), or a pharmaceutically acceptable salt thereof, wherein a compound of formula (2):

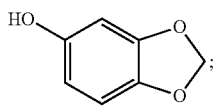

(2)

or a pharmaceutically acceptable salt thereof, is treated with a Grignard reagent of formula (3):

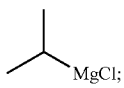

(3)

under suitable conditions to form an intermediate product; and the intermediate product is then reacted with a compound of formula (1):

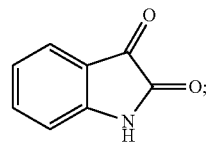

(1)

or a pharmaceutically acceptable salt thereof, under suitable conditions to form the compound of formula (4), or a pharmaceutically acceptable salt thereof.

Of the method of preparing a compound of formula (II), as set forth above in the Summary of the Invention, or a pharmaceutically acceptable salt thereof, as a single stereoisomer or enantiomer or a mixture thereof, one embodiment is the method which further comprises the preparation of a compound of formula (15), or a pharmaceutically acceptable salt thereof, wherein a compound of formula (14):

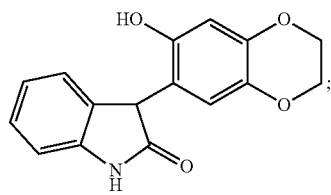

(14)

or a pharmaceutically acceptable salt thereof, is treated with an alkylating agent under suitable conditions to form the compound of formula (15), or a pharmaceutically acceptable salt thereof.

Of this embodiment, another embodiment is a method which further comprises the preparation of the compound of formula (14), or a pharmaceutically acceptable salt thereof, wherein a compound of formula (13):

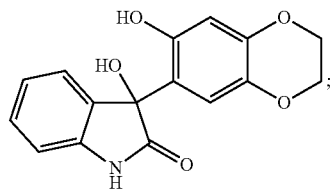

(13)

or a pharmaceutically acceptable salt thereof, is treated under suitable conditions to form the compound of formula (14), or a pharmaceutically acceptable salt thereof.

Of this embodiment, another embodiment is a method which further comprises the preparation of the compound of formula (13), or a pharmaceutically acceptable salt thereof, wherein a compound of formula (12):

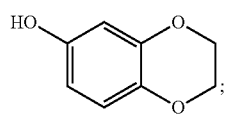

(12)

is reacted with a Grignard reagent of formula (3):

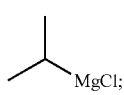

(3)

under suitable conditions to form an intermediate product; and then the intermediate product is reacted with a compound of formula (1):

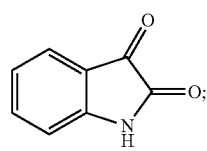

(1)

or a pharmaceutically acceptable salt thereof, under suitable conditions to form the compound of formula (13), or a pharmaceutically acceptable salt thereof.

Of this embodiment, another embodiment is a method which further comprises the preparation of the compound of formula (12), or a pharmaceutically acceptable salt thereof, wherein a compound of formula (11):

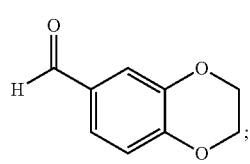

(11)

is treated with an oxidizing agent under suitable conditions to form the compound of formula (12), or a pharmaceutically acceptable salt thereof.

Of this embodiment, another embodiment is a method which further comprises the preparation of the compound of formula (11), wherein a compound of formula (10):

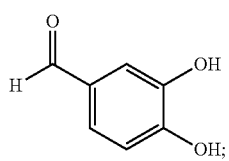

(10)

is treated with a suitable alkylating reagent under suitable conditions to form the compound of formula (11).

Specific embodiments of the methods of the invention, including the suitable conditions for each of the above described steps, are described in more detail below in the Methods of the Invention.

METHODS OF THE INVENTION

The methods of the invention are directed to methods of preparing compounds of formulae (I) and (II) and the compounds of formulae (I-S), (I-R), (II-S) and/or (II-R), as described herein, or pharmaceutically acceptable salts thereof.

In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *Advanced Organic Chemistry: Reactions, Mechanisms, and Structure,* 5th edition (Wiley, December 2000)) or prepared as described herein or by the methods disclosed in PCT Published Patent Application No. WO 2006/110917, PCT Published Patent Application No. WO 2010/45251 and PCT Patent Application No. PCT/US2010/040187.

Preparation of Compounds of Formulae (I), (I-S) and (I-R)

Compounds of formulae (I), (I-S) and (I-R) are prepared as described below in Reaction Scheme 1:

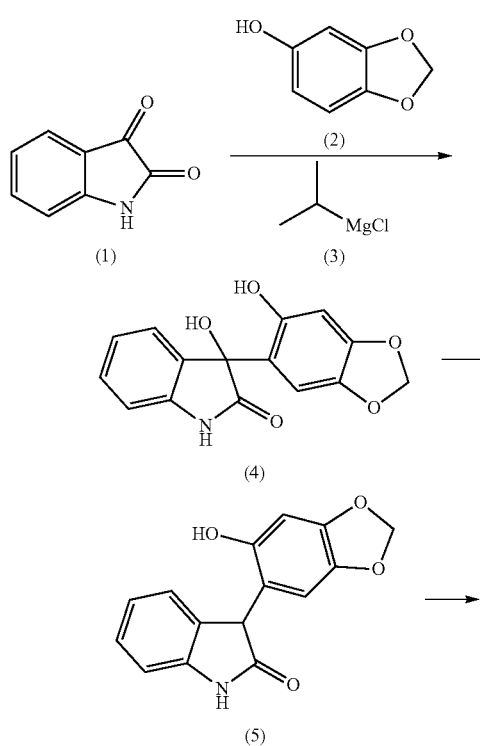
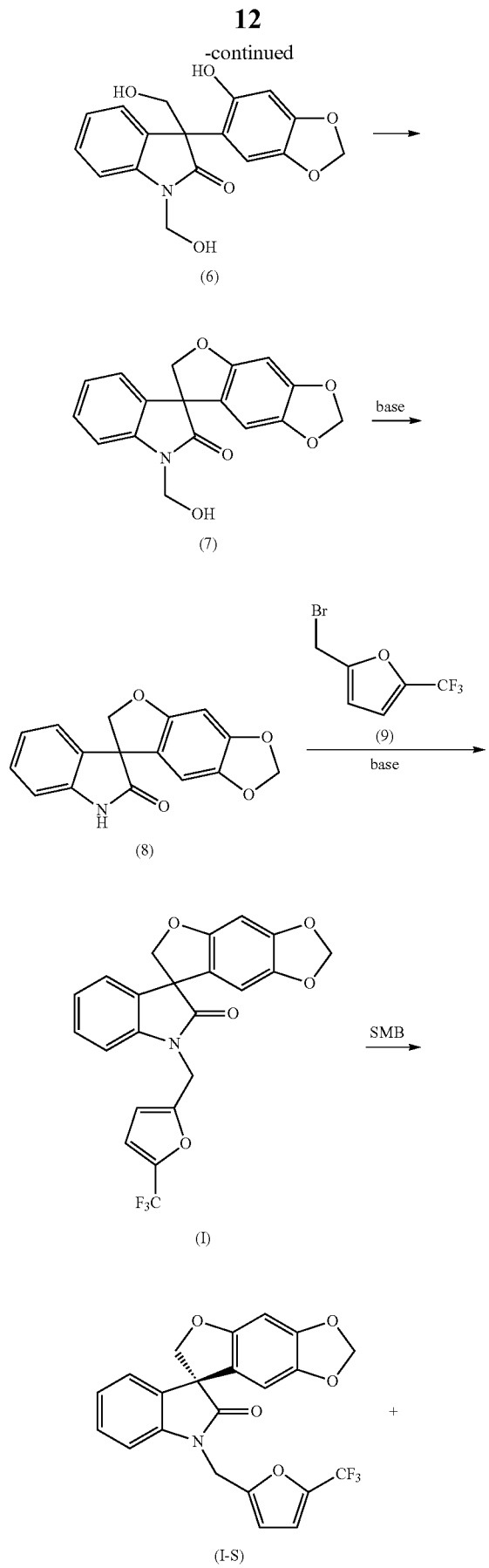

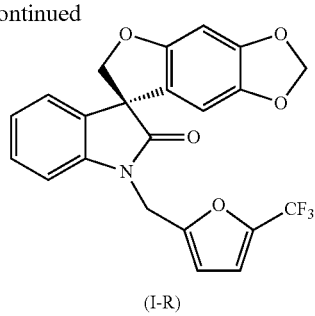

(I-R)

Compounds of formula (1), formula (2), formula (3) and formula (9) are commercially available, or can be prepared by methods known to one skill in the art.

In general, compounds of formula (I), (I-S) and (I-R) are prepared by the method disclosed above in Reaction Scheme 1 by first reacting a compound of formula (2) with a suitable Grignard reagent (such as that of formula (3)) under suitable conditions, such as at a temperature of between about −25° C. and about 25° C., preferably at about 0° C., to allow for the formation of a magnesium halide intermediate product. This intermediate product undergoes nucleophilic addition with the keto-carbonyl group of the isatin compound of formula (1) under suitable conditions, such as in a solvent, preferably, but not limited to, tetrahydrofuran or dichloromethane, to afford the oxindole compound of formula (4).

The removal of the hydroxyl group at the C-3 position of the oxindole ring in the compound of formula (4) is achieved by treating the compound of formula (4) under suitable conditions, such as treatment with a silane reagent, such as triethylsilane, in the presence of an acid, such as, but not limited to, trifluoroacetic acid, to yield the compound of formula (5). The removal of the hydroxyl group can also be achieved by treating the compound of formula (4) under suitable conditions, such as treatment with $SOCl_2/NEt_3$, followed by reduction of the resulting intermediate with Zn dust, to give the compound of formula (5). Alternatively, the removal can be achieved by treating the compound of formula (4) with hydriodic acid to give the compound of formula (5).

The compound of formula (5) is then treated under suitable conditions, such as treatment with a base, preferably, but not limited to, diisopropylamine, diisopropylethyl amine, lithium diisopropylamide, lithium hydroxide or sodium hydroxide, followed by reaction with formaldehyde or paraformaldehyde, to yield the hydroxymethyl intermediate compound of formula (6).

Intramolecular cyclization of the compound of formula (6) to yield the compound of formula (7) is achieved by treating the compound of formula (6) to standard Mitsunobu reaction conditions, such as the employment of a phosphine reagent, preferably, but not limited to, triphenylphosphine or tributylphosphine, and an azo reagent, preferably, but not limited to, diethyl azodicarboxylate, diisopropyl azodicarboxylate, di-tert-butyl azodicarboxylate or tetramethyl diazenedicarboxamide, in a solvent, preferably, but not limited to, tetrahydrofuran, dichloromethane or ethyl acetate. The resulting compound of formula (7) can be isolated from the reaction mixture by standard isolation techniques or used directly in the next step without being isolated from the reaction mixture.

Alternatively, intramolecular cyclization is achieved by treating the compound of formula (6) with a suitable bis-electrophile such as, but not limited to, chloroiodomethane in the presence of a base such as, but not limited to, cesium carbonate in a suitable solvent such as, but not limited to, N,N-dimethylformamide or methyl ethyl ketone to provide a compound of formula (8).

The removal of the hydroxymethyl group on the nitrogen of the compound of formula (7) is achieved by treating the compound of formula (7) with a base, preferably, but not limited to, sodium hydroxide, lithium hydroxide or ammonium hydroxide, under suitable conditions to provide a compound of formula (8), which can be isolated from the reaction mixture by standard isolation techniques.

The compound of formula (8) is then reacted with an electrophile of formula (9) under suitable conditions, such as in the presence of a base, preferably, but not limited to, sodium hydride, cesium carbonate or sodium hydroxide, in a solvent, preferably, but not limited to, N,N-dimethylformamide, acetonitrile, tetrahydrofuran or acetone, to yield the compound of formula (I), which can be isolated from the reaction mixture by standard isolation techniques.

The compound of formula (I) can be resolved into the (S)-enantiomer (i.e., the compound of formula (I-S)) and the corresponding (R)-enantiomer (i.e., the compound of formula (I-R)) under suitable conditions, for example, by chiral chromatographic separation such as, but not limited to, simulated moving bed chromatography or chiral HPLC.

Preparation of Compounds of Formulae (II), (II-S) and (II-R)

Compounds of formula (II), (II-S) and (II-R) are prepared as described below in Reaction Scheme 2:

REACTION SCHEME 2

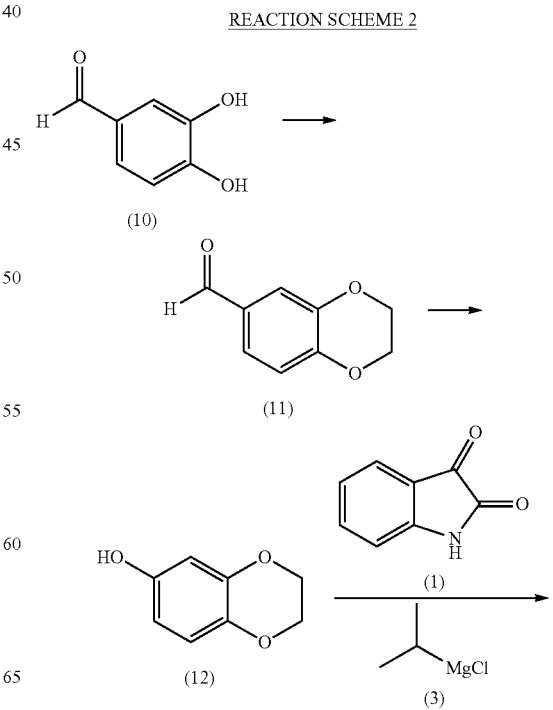

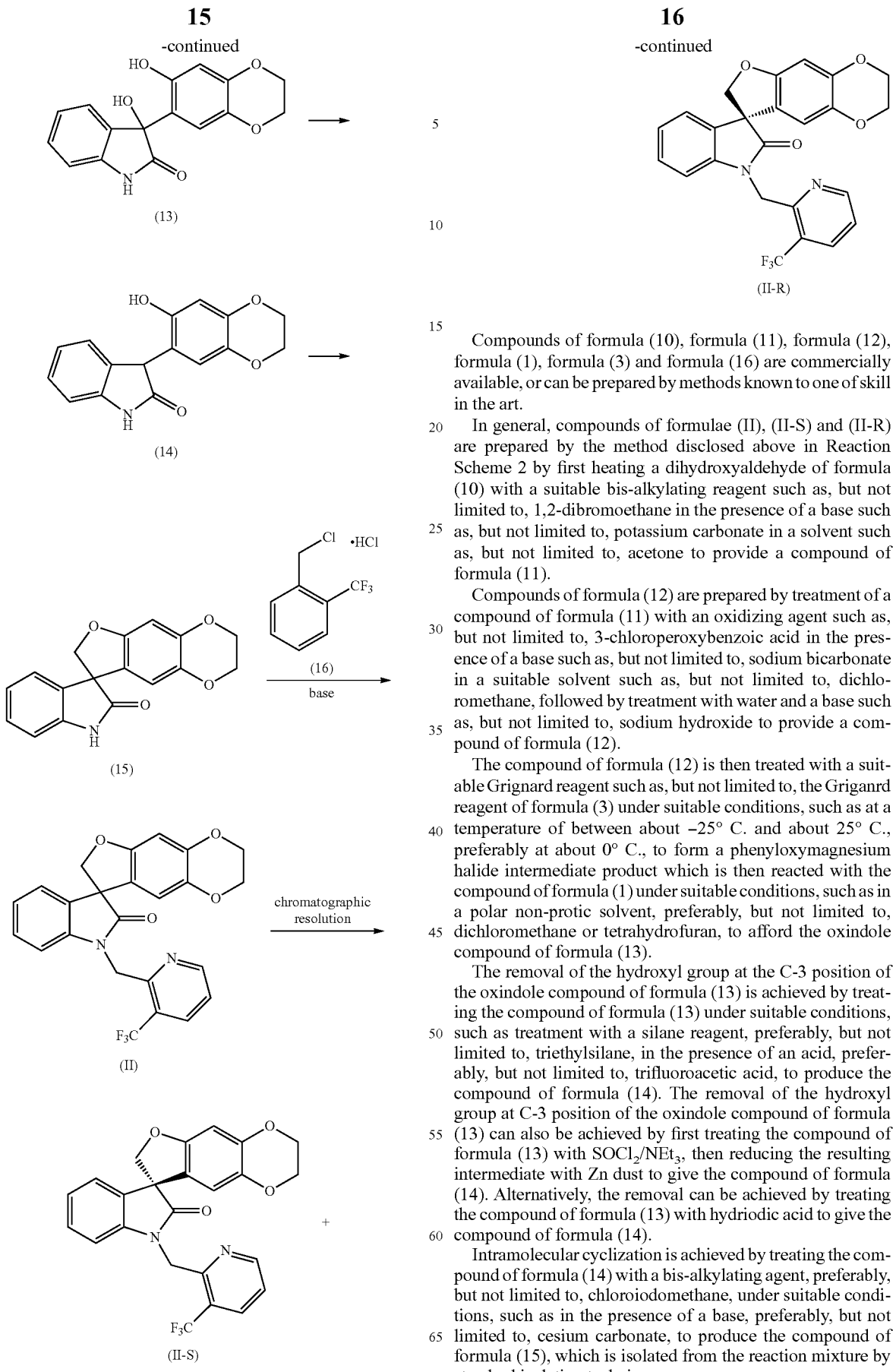

Compounds of formula (10), formula (11), formula (12), formula (1), formula (3) and formula (16) are commercially available, or can be prepared by methods known to one of skill in the art.

In general, compounds of formulae (II), (II-S) and (II-R) are prepared by the method disclosed above in Reaction Scheme 2 by first heating a dihydroxyaldehyde of formula (10) with a suitable bis-alkylating reagent such as, but not limited to, 1,2-dibromoethane in the presence of a base such as, but not limited to, potassium carbonate in a solvent such as, but not limited to, acetone to provide a compound of formula (11).

Compounds of formula (12) are prepared by treatment of a compound of formula (11) with an oxidizing agent such as, but not limited to, 3-chloroperoxybenzoic acid in the presence of a base such as, but not limited to, sodium bicarbonate in a suitable solvent such as, but not limited to, dichloromethane, followed by treatment with water and a base such as, but not limited to, sodium hydroxide to provide a compound of formula (12).

The compound of formula (12) is then treated with a suitable Grignard reagent such as, but not limited to, the Griganrd reagent of formula (3) under suitable conditions, such as at a temperature of between about −25° C. and about 25° C., preferably at about 0° C., to form a phenyloxymagnesium halide intermediate product which is then reacted with the compound of formula (1) under suitable conditions, such as in a polar non-protic solvent, preferably, but not limited to, dichloromethane or tetrahydrofuran, to afford the oxindole compound of formula (13).

The removal of the hydroxyl group at the C-3 position of the oxindole compound of formula (13) is achieved by treating the compound of formula (13) under suitable conditions, such as treatment with a silane reagent, preferably, but not limited to, triethylsilane, in the presence of an acid, preferably, but not limited to, trifluoroacetic acid, to produce the compound of formula (14). The removal of the hydroxyl group at C-3 position of the oxindole compound of formula (13) can also be achieved by first treating the compound of formula (13) with SOCl$_2$/NEt$_3$, then reducing the resulting intermediate with Zn dust to give the compound of formula (14). Alternatively, the removal can be achieved by treating the compound of formula (13) with hydriodic acid to give the compound of formula (14).

Intramolecular cyclization is achieved by treating the compound of formula (14) with a bis-alkylating agent, preferably, but not limited to, chloroiodomethane, under suitable conditions, such as in the presence of a base, preferably, but not limited to, cesium carbonate, to produce the compound of formula (15), which is isolated from the reaction mixture by standard isolation techniques.

The compound of formula (15) is then reacted with an electrophile of formula (16) under suitable conditions, such as in the presence of a base, preferably, but not limited to, sodium hydride, cesium carbonate or sodium hydroxide, in a solvent, preferably, but not limited to, N,N-dimethylformamide, acetonitrile, tetrahydrofuran, 1,4-dioxane or acetone, to yield the compound of formula (II), which can be isolated from the reaction mixture by standard isolation techniques.

The compound of formula (II) may be chromatographically resolved into the (S)-enantiomer (i.e., the compound of formula (II-S)) and the corresponding (R)-enantiomer (i.e., the compound of formula (II-R)) by simulated moving bed chromatography using a suitable chiral stationary phase such as, but not limited to, ChiralPAK®-IC and a suitable mobile phase such as, but not limited to, dichloromethane/acetone.

All of the compounds described above as being prepared which may exist in free base or acid form may be converted to their pharmaceutically acceptable salts by treatment with the appropriate inorganic or organic base or acid. Salts of the compounds prepared above may be converted to their free base or acid form by standard techniques. It is understood that all polymorphs, amorphous forms, anhydrates, hydrates, solvates and salts of the compounds of formula (I) and (II) are intended to be within the scope of the invention. Furthermore, all compounds of formula (I) and (II) which contain an acid or an ester group can be converted to the corresponding ester or acid, respectively, by methods known to one skilled in the art or by methods described herein.

The following specific Synthetic Preparations (for the preparation of starting materials and intermediates) and Synthetic Examples (for the preparation of the compounds of formula (I) and formula (II) by the methods of the invention) are provided as a guide to assist in the practice of the invention, and are not intended as a limitation on the scope of the invention. Where one or more NMR's are given for a particular compound, each NMR may represent a single stereoisomer, a non-racemic mixture of stereoisomers or a racemic mixture of the stereoisomers of the compound.

Synthetic Preparation 1

Synthesis of 3-hydroxy-3-(6-hydroxy-1,3-benzodioxol-5-yl)-1,3-dihydro-2H-indol-2-one Compound of Formula (4)

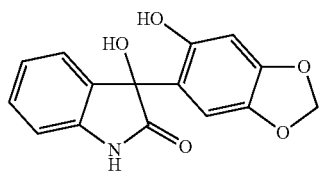 [SMILES: O=C1Nc2ccccc2C1(O)c1cc2c(cc1O)OCO2]

A 630 L reactor was charged with sesamol (42.6 kg, 299 mol). Tetrahydrofuran (400 kg) was added and the resultant solution was cooled to 1° C. over 42 minutes. Isopropylmagnesium chloride (2 M solution in tetrahydrofuran, 173 kg, 337 mol) was added over 2 h such that the internal temperature was kept between 0 and 4° C. Once the addition was complete, the internal temperature was lowered to −5° C. and isatin (37.9 kg, 250 mol) was added in four portions. The reaction mixture was stirred for 2.75 h at 1 to 3° C. A 1000 L reactor was charged with ammonium chloride (72 kg), followed by deionized water (356 kg). The mixture was stirred at 15° C. until the solid had completely dissolved and the resultant solution was cooled to 1° C. over 1 h. The contents of the 630 L reactor were transferred to the 1000 L reactor over 1 h such that the internal temperature remained between 3 and 4° C. The 630 L reactor was rinsed with toluene (133 kg) and the rinse solution added to the 1000 L reactor. The contents of the 1000 L reactor were allowed to warm to 20-25° C. over 29 minutes and were stirred for a further 15 minutes. The stirring was stopped and the contents of the reactor held at 25° C. for 15 minutes, allowing the phases to separate. The aqueous phase was removed and a solution of sodium chloride (42 kg) in deionized water (218 kg) was added over 25 minutes at an internal temperature of 22-24° C. The stirring was stopped and the mixture held at 25° C. for 1 h, allowing the phases to separate. The organic phase was degassed for 0.5 h with nitrogen and toluene (89 kg) was added. A 300 mbar vacuum was applied to the reactor and the reactor's external temperature was set to 50-60° C. Volatile components of the mixture were removed by distillation over a period of 12 h such that 670 L of distillate were collected. The reactor's external temperature was set to 20-25° C. An orange precipitate was deposited upon cooling. Toluene (114 kg) was added and the suspension stirred for 10 minutes. The solid was collected by filtration, washed with tert-butyl methyl ether (171 kg) and heptane (85 kg) and dried at 55-60° C. under a reduced pressure of 170 to 4 mbar over a period of 10.5 h to afford 3-hydroxy-3-(6-hydroxy-1,3-benzodioxol-5-yl)-1,3-dihydro-2H-indol-2-one (73.5 kg, quantitative yield) as a pale pink solid: purity (HPLC-UV at 300 nm) 99.3% a/a; $^1$H NMR (300 MHz, DMSO-$d_6$) δ 10.18 (s, 1H), 9.08 (s, 1H), 7.21-7.07 (m, 2H), 6.88-6.74 (m, 3H), 6.38 (br s, 1H), 6.23 (s, 1H), 5.92 (s, 2H); $^{13}$C NMR (75 MHz, DMSO-$d_6$) δ 178.4, 148.4, 146.6, 143.0, 139.4, 133.2, 128.6, 123.8, 121.1, 120.1, 109.0, 106.8, 100.8, 97.4, 75.1.

Synthetic Preparation 2

Synthesis of 3-(6-hydroxy-1,3-benzodioxol-5-yl)-1,3-dihydro-2H-indol-2-one

Compound of Formula (5)

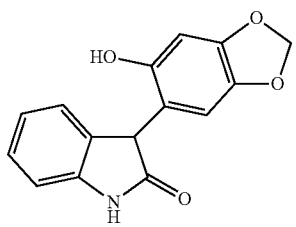 [SMILES: O=C1Nc2ccccc2C1c1cc2c(cc1O)OCO2]

A 1600 L reactor was charged with 3-hydroxy-3-(6-hydroxy-1,3-benzodioxol-5-yl)-1,3-dihydro-2H-indol-2-one (113.1 kg, 396 mol), evacuated and filled with nitrogen. Trifluoroacetic acid (679 kg) was added in two portions over 20 minutes and the internal temperature was lowered to 10° C. over 1 h. Triethylsilane (69.2 kg, 595 mol) was added over 2 h 05 min at 10-11° C. and the mixture was stirred for a further 0.5 h at 10-11° C. A 1000 L reactor was charged with heptane (524 kg) and tert-butyl methyl ether (63 kg). The contents of the 1000 L reactor were transferred to the 1600 L reactor over 13 minutes at an internal temperature of 10-11° C. The resultant yellow-orange suspension was allowed to warm to 23° C. over 1 h. The solid was collected by filtration, washed with heptane (464 kg) followed by tert-butyl methyl ether (57 kg) and dried at 50° C. under a reduced pressure of 58 to 7 mbar over a period of 25 h to afford 3-(6-hydroxy-1,3-benzodioxol-5-yl)-1,3-dihydro-2H-indol-2-one (82.8 kg, 75%) as an off-white solid: purity (HPLC-UV at 300 nm) 98.0% a/a; $^1$H NMR (300 MHz, DMSO-$d_6$) δ 10.40 (s, 1H), 9.25 (s, 1H), 7.17-7.10 (m, 1H), 6.95-6.81 (m, 3H), 6.55 (s, 1H), 6.43 (s, 1H), 5.92-5.85 (m, 2H), 4.66 (s, 1H); $^{13}$C NMR (75 MHz, DMSO-$d_6$) δ 177.9, 150.1, 146.6, 142.7, 139.6, 130.9, 127.4, 123.8, 121.2, 115.9, 109.5, 109.0, 100.7, 97.8, 55.0.

Synthetic Preparation 3

Synthesis of 3-(6-hydroxy-1,3-benzodioxol-5-yl)-1,3-bis(hydroxymethyl)-1,3-dihydro-2H-indol-2-one Compound of Formula (6)

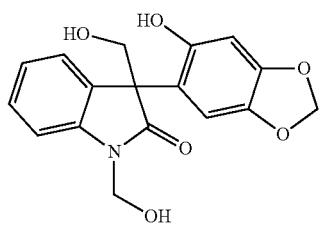 [SMILES: O=C1N(CO)c2ccccc2C1(CO)c1cc2c(cc1O)OCO2]

A 1000 L reactor was charged with 3-(6-hydroxy-1,3-benzodioxol-5-yl)-1,3-dihydro-2H-indol-2-one (56.3 kg, 209 mol), followed by paraformaldehyde (25.4 kg, 847 mol) and deionized water (285 kg). The reaction mixture was cooled to an internal temperature of 5° C. over 25 minutes and a 30% by weight aqueous solution of sodium hydroxide (113 kg, 847 mol) was added at 5° C. over 40 minutes. The reaction mixture was stirred for 1 h at 5° C. A second 1000 L reactor was charged with deionized water (260 kg) and 32% hydrochloric acid (124 kg). The contents of the first reactor were added to the contents of the second reactor at 1° C. over 80 minutes. The first reactor was rinsed with deionized water (35 kg) and the rinse solution transferred to the second reactor. The resultant suspension was stirred for at 1° C. for 1 h and the solid was collected by filtration, washed with a mixture of concentrated hydrochloric acid (11 kg) and water (20 kg) and dried at 55-60° C. under a reduced pressure of 50 to 6 mbar over a period of 24 h to afford 3-(6-hydroxy-1,3-benzodioxol-5-yl)-1,3-bis(hydroxymethyl)-1,3-dihydro-2H-indol-2-one (69.8 kg, 99%) as a pale brown solid: purity (HPLC-UV at 230 nm) 95.4% a/a; $^1$H NMR (DMSO-$d_6$, 300 MHz) δ 9.06 (s, 1H), 7.17-6.84 (m, 5H), 6.19-6.10 (m, 2H), 5.86 (s, 2H), 5.12-4.92 (m, 3H), 4.11-4.06 (m, 1H), 3.79-3.73 (m, 1H); $^{13}$C NMR (DMSO-$d_6$, 75 MHz) δ 179.0, 150.5, 146.7, 143.9, 139.9, 132.6, 127.4, 124.0, 121.9, 118.2, 108.7, 108.6, 101.1, 98.0, 65.4, 63.2, 56.2.

Synthetic Preparation 4

Synthesis of spiro[furo[2,3-f][1,3]benzodioxole-7,3'-indol]-2'(1'H)-one

Compound of Formula (8)

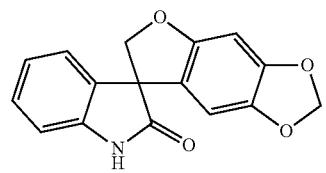 [SMILES: O=C1Nc2ccccc2C12COc1cc3c(cc12)OCO3]

A 1000 L reactor was charged with 3-(6-hydroxy-1,3-benzodioxol-5-yl)-1,3-bis(hydroxymethyl)-1,3-dihydro-2H-indol-2-one (65.0 kg, 197 mol), followed by tetrahydrofuran (586 kg). The resultant solution was cooled to −4° C. over 20 minutes and tri-n-butylphosphine (40.0 kg, 197 mol) was added over 6 minutes, followed by a solution of diisopropyl azodicarboxylate (44.8 kg, 197 mol) in tetrahydrofuran (75 kg) over 125 minutes such that the internal temperature remained below 0° C. The reaction mixture was stirred at −3° C. for a further 25 minutes and the contents of the reactor were transferred to a 2500 L reactor. The 1000 L reactor was rinsed with tetrahydrofuran (16 kg) and the rinse solution added to the 2500 L reactor. A 25% by weight solution of ammonia in water (118 kg) was added at −3 to −2° C. over 30 minutes. The reaction mixture was allowed to warm to 25° C. over 1.25 h and was stirred for a further 2 h. Deionized water (650 kg) and ethyl acetate (585 kg) were added and the mixture was warmed to 40° C. over 40 minutes. After stirring for a further 15 minutes, the stirring was stopped and the phases were allowed to separate for 1 h. The aqueous phase was removed and deionized water (650 kg) was added. The mixture was stirred for 15 minutes at 40° C. The stirring was stopped and the phases were allowed to separate for 1 h. The aqueous phase was removed and deionized water (325 kg) was added. The mixture was partially concentrated by distillation under reduced pressure at an internal temperature of 21-39° C. and a pressure of 382 to 98 mbar until 950 L of distillate had been collected over a period of 4.5 h. Methanol (1600 kg) was added and the mixture heated to 60° C. over 35 minutes. The mixture was partially concentrated by distillation under reduced pressure at an internal temperature of 32-58° C. and a pressure of 530 to 170 mbar until 1260 L of distillate had been collected over a period of 9.33 h. The resultant suspension was allowed to cool to 22° C. over 2 h and was stirred for a further 6 h. The solid was collected by filtration, washed with a mixture of methanol (34 kg) and deionized water (17 kg) and dried at 55-60° C. under a reduced pressure of 50 to 3 mbar over a period of 31 h to afford 35.8 kg of a brown solid, which was transferred to a 400 L reactor. Methanol (163 kg) was added and the resultant suspension was stirred for 0.5 h. The mixture was heated to reflux over a period of 35 minutes and was heated at reflux for a further 15 minutes. Deionized water (33 kg) was added and the mixture was heated at reflux for 155 minutes. The suspension was filtered while hot and the filter cake was washed with a mixture of methanol (22 kg)

and deionized water (11 kg) and dried at 55-60° C. under a reduced pressure of 50 to 4 mbar over a period of 8 h to afford spiro[furo[2,3-t][1,3]benzodioxole-7,3'-indol]-2'(1'H)-one (30.44 kg, 49%) as a pale brown solid: purity (HPLC-UV at 230 nm) 89.4%; MS (ES+) m/z 282.3 (M+1); $^1$H NMR (400 MHz, CDCl$_3$) δ10.56 (s, 1H), 7.27-6.92 (m, 4H), 6.67 (s, 1H), 6.26 (s, 1H), 5.93 (s, 2H), 4.79-4.64 (m, 2H).

Synthetic Preparation 5

Synthesis of 2,3-dihydro-1,4-benzodioxine-6-carbaldehyde

Compound of Formula (11)

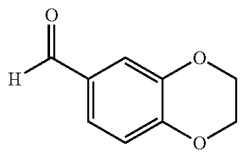

A 2000 L reactor was charged with acetone (404.5 kg), followed by potassium carbonate (256 kg, 1852 mol) and 1,2-dibromoethane (241.5 kg, 1298 mol). The mixture was heated at reflux. A 500 L reactor was charged with acetone (606 kg) and 3,4-dihydroxybenzalhdehyde (128 kg, 926 mol). The contents of the 500 L reactor were added to the 2000 L reactor at a rate of 150-180 kg/h while the reaction temperature was maintained at 50-60° C. The reaction mixture was stirred at 54-60° C. for 12 h, was cooled to 20° C. and was filtered through a 500 L Nutsche filter. The filter cake was washed with acetone (2×202 kg). The filtrate and acetone washes were combined in a 2000 L reactor and the resultant solution was concentrated to dryness under reduced pressure at a temperature <40° C. To the residue was added ethyl acetate (683 kg) and the resultant solution was washed with a 5% by weight aqueous solution of potassium carbonate (256 kg). The mixture was stirred for 0.5 h, allowed to settle for 0.5 h and the aqueous phase was removed. This washing procedure was repeated three times in total. The organic phase was temporarily set aside into drums. A 2000 L reactor was charged with the combined aqueous washes, followed by ethyl acetate (113.9 kg). The mixture was stirred for 0.5 h, allowed to settle for 0.5 h and the aqueous phase was removed. The organic phase from the drums was added to the reactor followed by a 28% by weight aqueous solution of sodium chloride (192 kg). The mixture was stirred for 0.5 h, allowed to settle for 0.5 h and the aqueous phase was removed. The organic phase was concentrated under reduced pressure at a temperature <45° C. until the mixture's ethyl acetate content was below 10% (as determined by gas chromatography). Petroleum ether (268.8 kg) was added to the residue at a rate of 80-90 kg/h while the mixture was maintained at a temperature of 35-45° C. The mixture was cooled to 5° C. over 3 h and held at this temperature for a further 1 h, during which time a precipitate was deposited. The resultant slurry was filtered through a centrifugal filter and dried to afford 2,3-dihydro-1,4-benzodioxine-6-carbaldehyde (111.4 kg, 73%) as an off-white solid: purity (HPLC-UV at 230 nm) 99.3%.

Synthetic Preparation 6

Synthesis of 2,3-dihydro-1,4-benzodioxin-6-ol

Compound of Formula (12)

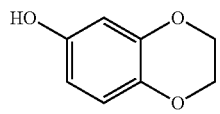

A 2000 L reactor was charged with dichloromethane (1303.4 kg) followed by 2,3-dihydro-1,4-benzodioxine-6-carbaldehyde (98.0 kg, 597 mol) and stirred until a homogeneous solution was obtained. 3-Chloroperoxybenzoic acid (144.3 kg, 836 mol) was added. The mixture was heated to reflux at a rate of 8-10° C./h, heated at reflux for a further 6 h and allowed to cool to 20° C. The resultant suspension was filtered through a 500 L Nutsche filter and the filter cake was washed with dichloromethane (391 kg). The filtrate and wash solution were transferred to a 2000 L reactor. A 7% by weight aqueous solution of sodium bicarbonate (212.7 kg) was added and the mixture was stirred for 0.5 h. The stirring was stopped and the phases were allowed to separate over 0.5 h. The aqueous layer was removed. The aqueous sodium bicarbonate washing procedure was repeated three times in total. The organic phase was concentrated to dryness under reduced pressure at a temperature <30° C. Methanol (116.1 kg) was added and the resultant mixture was cooled to 0° C. A 15.5% by weight aqueous solution of sodium hydroxide (234.3 kg) was added at a rate of 30-40 kg/h such that the mixture's temperature was maintained between 0-10° C. The mixture was stirred at this temperature for a further 2.25 h and the pH of the mixture was adjusted to 6-7 by the addition of 4 N hydrochloric acid (266.5 kg) such that the mixture's temperature was maintained between 0-10° C. The mixture was allowed to warm to ambient temperature and was extracted three times in total with methyl tert-butyl ether (145 kg for each extraction) by stirring for 0.5 h, stopping the stirring and allowing the phases to separate for 0.5 h. The combined organic extracts were washed three times in total with a 7% aqueous solution of sodium bicarbonate (212.7 kg for each wash) by stirring for 0.5 h, stopping the stirring, allowing the phases to separate for 0.5 h and removing the aqueous phase. The organic phase was then washed with a 30% by weight aqueous solution of sodium chloride (212.7 kg) by stirring for 0.5 h, stopping the stirring, allowing the phases to separate for 0.5 h and removing the aqueous phase. The organic phase was concentrated to dryness under reduced pressure at a temperature <45° C. Tetrahydrofuran (170 kg) was added and the resultant solution concentrated to dryness under reduced pressure at a temperature <45° C. Further tetrahydrofuran (17.1 kg) was added and the resultant solution concentrated to dryness under reduced pressure at a temperature <45° C. Tetrahydrofuran (122.5 kg) was added to afford a brown-red solution of 2,3-dihydro-1,4-benzodioxin-6-ol (86.3 kg, 95%) in tetrahydrofuran which was carried forward without further purification: purity (HPLC-UV at 220 nm) 95.7%.

Synthetic Preparation 7

Synthesis of 3-hydroxy-3-(7-hydroxy-2,3-dihydro-1,4-benzodioxin-6-yl)-1,3-dihydro-2H-indol-2-one Compound of Formula (13)

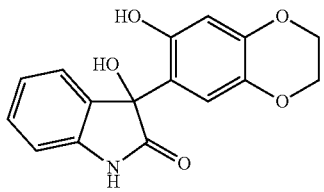 [SMILES: O=C1Nc2ccccc2C1(O)c1cc2c(cc1O)OCCO2]

A 1000 L reactor was charged with tetrahydrofuran (296.8 kg). The tetrahydrofuran was heated at reflux for 1 h and allowed to cool to ambient temperature. Magnesium (15.0 kg, 625 mol), iodine (19.5 g, catalytic amount) and bromoethane (147.0 g, catalytic amount) were added at a temperature of 15-30° C. The resultant mixture was heated at 50-55° C. for 0.5 h and 2-chloropropane (4.5 kg, 57 mol) was added, followed by a 2 M solution of isopropylmagnesium chloride in tetrahydrofuran (7.6 kg, catalytic amount). 2-Chloropropane (39.2 kg, 500 mol) was added at a rate of 8-10 kg/h such that the temperature of the reaction mixture was maintained between 55-70° C. The reaction mixture was heated at 58-68° C. for 3 h, allowed to cool to ambient temperature and was stirred for a further 4 h. A 2000 L reactor was charged with a solution of 2,3-dihydro-1,4-benzodioxin-6-ol (86.3 kg, 567 mol) in tetrahydrofuran (122.5 kg), followed by further tetrahydrofuran (804.1 kg). The resultant solution was cooled to 0° C. and the contents of the 1000 L reactor were added to the 2000 L reactor at a rate of 30-50 kg/h such that the temperature of the reaction mixture was maintained between 0-5° C. The 1000 L reactor was rinsed three times with tetrahydrofuran (5 kg for each rinse) and the rinse solutions were added to the 2000 L reactor. The reaction mixture was stirred at 7-13° C. for 1 h and was cooled to −5° C. Isatin (69.5 kg, 472.5 mol) was added in three equal portions over 0.5 h and the mixture stirred for 0.5 h at −5-0° C. The reaction mixture was heated at 50-55° C. for 7.5 h and was allowed to cool to ambient temperature. A 5000 L reactor was charged with water (576.9 kg) and ammonium chloride (118.2 kg). The resultant solution was cooled to 0-5° C. The contents of the 2000 L reactor were added to the 5000 L reactor at a rate of 300-500 kg/h such that the temperature of the mixture was maintained between 0-5° C. The mixture was stirred at 15-25° C. for 0.5 h and the stirring was stopped. The phases were allowed to separate for 1 h and the aqueous phase was removed. A 27% by weight aqueous solution of sodium chloride (69.6 kg) was added and the mixture stirred for 0.5 h. The stirring was stopped, the phases were allowed to separate for 1 h and the aqueous layer was removed. The aqueous sodium chloride wash procedure was repeated two times in total. The organic phase was transferred to a 2000 L reactor and was concentrated under reduced pressure at a temperature of 45-55° C. Toluene (302.3 kg) was added to the residue at a rate of 90-130 kg/h and at a temperature of 45-50° C. The resultant mixture was cooled to 15° C. at a rate of 8-10° C./h and stirred for at 10-15° C. for a further 1 h. The resultant slurry was filtered through a centrifugal filter and the filter cake was washed with water (69.5 kg) and dried at 45-50° C. to afford 3-hydroxy-3-(7-hydroxy-2,3-dihydro-1,4-benzodioxin-6-yl)-1,3-dihydro-2H-indol-2-one (130.8 kg, 93%) as an off-white solid: purity (HPLC-UV at 210 nm) 99.7%.

Synthetic Preparation 8

Synthesis of 3-(7-hydroxy-2,3-dihydro-1,4-benzodioxin-6-yl)-1,3-dihydro-2H-indol-2-one Compound of Formula (14)

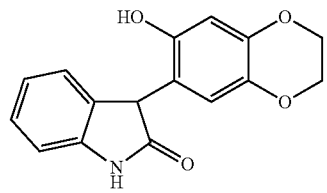 [SMILES: O=C1Nc2ccccc2C1c1cc2c(cc1O)OCCO2]

A 2000 L reactor was charged with dichloromethane (489.4 kg), followed by 3-hydroxy-3-(7-hydroxy-2,3-dihydro-1,4-benzodioxin-6-yl)-1,3-dihydro-2H-indol-2-one (92.0 kg, 307 mol) in four 23 kg portions over 1 h. The resultant solution was stirred at ambient temperature for 1 h and triethylsilane (107.2 kg, 921 mol) was added. The mixture was cooled to −5° C. and trifluoroacetic acid (105.1 kg, 921 mol) was added at a rate of 25-30 kg/h such that the temperature of the reaction mixture remained below 0° C. The mixture was stirred at −5-0° C. for 2.5 h, warmed to 18-20° C., stirred for a further 6.5 h and concentrated to dryness under reduced pressure at a temperature <30° C. Methyl tert-butyl ether (139.8 kg) was added to the residue at 15-20° C. and the mixture concentrated to near-dryness under reduced pressure at a temperature <35° C. The mixture was filtered in a centrifugal filter and a 2000 L reactor was charged with the filter cake, followed by methanol (72.7 kg). The mixture was stirred at 10-15° C. for 0.5 h and filtered in a centrifugal filter. The filter cake was dried under reduced pressure at 40-50° C. to afford 3-(7-hydroxy-2,3-dihydro-1,4-benzodioxin-6-yl)-1,3-dihydro-2H-indol-2-one (68.0 kg, 78%) as a colorless solid: purity (HPLC-UV at 254 nm) 99.3%.

Synthetic Preparation 9

Synthesis of 2,3-dihydrospiro[furo[2,3-g][1,4]benzodioxine-8,3'-indol]-2'(1'H)-one Compound of Formula (15)

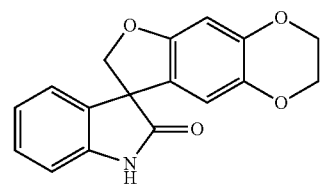 [SMILES: O=C1Nc2ccccc2C12COc1cc3c(cc12)OCCO3]

A 2000 L stainless steel crystallizer was charged with N,N-dimethylformamide (113.7 kg) and tetrahydrofuran (1070.9 kg). The contents were cooled to 0-5° C. and 3-(7-hydroxy-2,3-dihydro-1,4-benzodioxin-6-yl)-1,3-dihydro-2H-indol-2-one (12.0 kg, 42.4 mol) was added, followed by cesium carbonate (30.4 kg, 93.3 mol). A solution of chloroiodomethane (9.4 kg, 53.7 mol) in N,N-dimethylformamide (16.9 kg) was added at a rate of 39.5 kg/h such that the temperature of the reaction mixture was maintained between 0 and 5° C. The reaction mixture was stirred at 0-5° C. for 2 h and heated at 20-25° C. for 18.5 h. The mixture was filtered and the filter cake was suspended in tetrahydrofuran (26.4 kg) and filtered again. The combined filtrates were combined and concentrated to a volume of 110 L under reduced pressure at a temperature <60° C. The mixture was cooled to 20-25° C. and purified water (1200.8 kg) was added at a rate of 343.1 kg/h. The mixture was cooled to 0-5° C. and filtered. The filter cake was suspended in water (310.5 kg), filtered and dried at a temperature <60° C. until the water content was 10.6% by weight by Karl-Fisher titration. A 200 L reactor was charged with tetrahydrofuran (98.0 kg). The partially-dried filter cake (~11.0 kg) was added to the 200 L reactor by means of a solid addition funnel. The mixture was heated at reflux for 4.5 h, cooled to 10-15° C. and stirred for 3.5 h at 10-15° C. The mixture was filtered and the filter cake was washed with cold (0-5° C.) tetrahydrofuran (2×10.7 kg) and dried in a tray dryer at a temperature <55° C. to afford 2,3-dihydrospiro[furo[2,3-g][1,4]benzodioxine-8,3'-indol]-2'(1'H)-one (6.88 kg, 63%) as a pale yellow solid: purity (HPLC-UV at 210 nm) 98.3%; mp>250° C.; $^1$H NMR (300 MHz, DMSO-$d_6$) δ 10.58 (br s, 1H), 7.26-7.19 (m, 1H), 7.09 (d, J=7.2 Hz, 1H), 6.99-6.90 (m, 2H), 6.47 (s, 1H), 6.16 (s, 1H), 4.74, 4.60 (ABq, $J_{AB}$=9.2 Hz, 2H), 4.20-4.07 (m, 4H); $^{13}$C NMR (75 MHz, DMSO-$d_6$) δ 178.4, 154.7, 144.0, 141.8, 137.8, 132.6, 128.7, 123.8, 122.3, 121.5, 111.1, 109.8, 98.7, 79.5, 64.2, 63.6, 57.7; MS (ES+) m/z 295.9 (M+1).

Synthetic Example 1

Synthesis of 1'-{[5-(trifluoromethyl)-2-furyl]methyl}spiro[furo[2,3-f][1,3]benzodioxole-7,3'-indol]-2'(1'H)-one Compound of Formula (I)

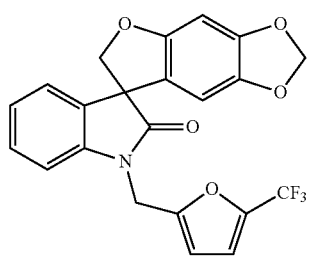 [SMILES: O=C1N(Cc2ccc(C(F)(F)F)o2)c2ccccc2C12COc1cc3c(cc12)OCO3]

A 100 L reactor was charged with spiro[furo[2,3-t][1,3]benzodioxole-7,3'-indol]-2'(1'H)-one (6.03 kg, 19.5 mol), followed by cesium carbonate (16.02 kg, 48.7 mol). Acetone (48.8 kg) was added and the resultant suspension was heated to reflux over 1 h. 2-Bromomethyl-5-(trifluoromethyl)furan (4.92 kg, 21.2 mol) was added by means of an addition funnel over a period of 2 h while the reaction mixture was maintained at reflux. The reaction mixture was stirred at reflux for a further 2 h and the acetone was removed by distillation at atmospheric pressure until 37 L of distillate had been collected. Toluene (48.8 kg) was added and the distillation was continued, first at atmospheric pressure then under reduced pressure until 37 L of distillate had been collected. Toluene (36.9 kg) was added and the distillation was continued at 54-55° C. and a pressure of 150-180 mbar until 37 L of distillate had been collected. The contents of the 100 L reactor were allowed to cool to 25° C. and toluene (40.9 kg) was added. The contents of the 100 L reactor were transferred to a 200 L reactor and deionized water (48.8 kg) was added. The stirred mixture was warmed to 39° C., the stirring was stopped and the phases were allowed to separate for 11 h. The lower phase was removed and the remaining toluene phase was subjected to distillation at 55-64° C. under a reduced pressure of 100 mbar until 18 L of distillate had been collected. The resultant solution was diluted with toluene to a total volume of 98 L. The contents of the 200 L reactor were passed through a chromatography column packed with silica gel (20 kg) and toluene (40 kg). The column was eluted with toluene such that ten 30 kg fractions were collected. The column was washed with acetone (100 kg). Fractions 2 through 10 were successively transferred to a 200 L reactor as a distillation under reduced pressure was proceeding. The contents of the reactor were adjusted with toluene to a volume of 50 L and the solution was heated to 79° C. Heptane (85 kg) was added over 15 minutes and the mixture was cooled to 10° C. over a period of 3 h. Crystallization started at an internal temperature of 56° C. The solid was collected by filtration, washed with a mixture of heptane (10.2 kg) and toluene (5.1 kg) and dried at 45-50° C. under a reduced pressure of 50 mbar over a period of 15 h to afford 1'-{[5-(trifluoromethyl)-2-furyl]methyl}spiro[furo[2,3-f][1,3]benzodioxole-7,3'-indol]-2'(1'H)-one (6.08 kg, 73%) as a colorless solid: purity (HPLC-UV at 230 nm) 99.6%; mp 139-141° C.; $^1$H NMR (300 MHz, CDCl$_3$) δ 7.32-6.97 (m, 5H), 6.72 (d, J=3.3 Hz, 1H), 6.66 (s, 1H), 6.07 (s, 1H), 5.90-5.88 (m, 2H), 5.05, 4.86 (ABq, $J_{AB}$=16.1 Hz, 2H), 4.91 (d, J=9.0 Hz, 1H), 4.66 (d, J=9.0 Hz, 1H); $^{13}$C NMR (75 MHz, CDCl$_3$) δ 176.9, 155.7, 153.5, 148.8, 142.2, 141.9, 140.8, 140.2, 139.7, 139.1, 132.1, 129.2, 124.7, 124.1, 123.7, 121.1, 120.1, 117.6, 114.5, 114.4, 110.3, 109.7, 103.0, 101.9, 93.8, 80.0, 57.8, 36.9; MS (ES+) m/z 430.2 (M+1), 452.2 (M+23); Calc'd for $C_{22}H_{14}F_3NO_5$: C, 61.54%; H, 3.29%; N, 3.26%. Found: C, 61.51%; H, 3.29%; N, 3.26%.

Synthetic Example 2

Resolution of Compound of Formula (I) by Chiral HPLC

The compound of formula (I) was resolved into the compound of formula (I-S) and the compound of formula (I-R) by chiral HPLC under the following conditions:
  Column: Chiralcel® OJ-RH; 20 mm I.D.×250 mm, 5 mic; Lot: OJRH CJ-EH001 (Daicel Chemical Industries, Ltd)
  Eluent: Acetonitrile/Water (60/40, v/v, isocratic)
  Flow rate: 10 mL/min
  Run time: 60 min
  Loading: 100 mg of compound of formula (I) in 1 mL of acetonitrile
  Temperature: Ambient Under the above chiral HPLC conditions, the compound of formula (I-R), i.e., (R)-1'-{[5-(trifluoromethyl)furan-2-yl]methyl}spiro[furo[2,3-f][1,3]-benzodioxole-7,3'-indol]-2'(1'H)-one, was isolated as the first fraction as a white solid; ee (enantiomeric excess)>99% (analytical OJ-RH, 55% acetonitrile in water); mp 103-105° C.; $^1$H NMR (300 MHz, DMSO-$d_6$) δ 7.32-6.99 (m, 5H), 6.71 (d, J=3.4 Hz, 1H), 6.67 (s, 1H), 6.05 (s, 1H), 5.89 (d, J=6.2 Hz, 2H), 5.13, 5.02 (ABq, $J_{AB}$=16.4 Hz, 2H), 4.82, 4.72 (ABq, $J_{AB}$=9.4 Hz, 2H); $^{13}$C NMR (75 MHz, CDCl$_3$) δ 177.2, 155.9, 152.0, 149.0, 142.4, 142.0, 141.3, 132.0, 129.1, 123.9, 120.6, 119.2, 117.0, 112.6, 109.3, 108.9, 103.0, 101.6, 93.5, 80.3, 58.2, 36.9; MS (ES+)

m/z 430.2 (M+1), [α]$_D$ −17.46° (c 0.99, DMSO). The compound of formula (I-S), i.e., (S)-1'-{[5-(trifluoromethyl)furan-2-yl]methyl}spiro-[furo[2,3-f][1,3]benzodioxole-7,3'-indol]-2'(1'H)-one, was isolated as the second fraction as a white solid; ee>99% (analytical OJ-RH, 55% acetonitrile in water); mp 100-102° C.; $^1$H NMR (300 MHz, DMSO-d$_6$) δ 7.32-6.99 (m, 5H), 6.71 (d, J=3.4 Hz, 1H), 6.67 (s, 1H), 6.05 (s, 1H), 5.89 (d, J=6.3 Hz, 2H), 5.12, 5.02 (ABq, J$_{AB}$=16.4 Hz, 2H), 4.82, 4.72 (ABq, J$_{AB}$=9.4 Hz, 2H); $^{13}$C NMR (75 MHz, CDCl$_3$) δ 177.2, 155.9, 152.0, 149.0, 142.4, 142.0, 141.3, 132.0, 129.1, 123.9, 120.6, 119.2, 117.0, 112.6, 109.3, 108.9, 103.0, 101.6, 93.5, 80.3, 58.2, 36.9; MS (ES+) m/z 430.2 (M+1), [α]$_D$ +14.04° (c 0.99, DMSO).

Synthetic Example 3

Resolution of Compound of Formula (I) by SMB Chromatography

The compound of formula (1) was resolved into the compound of formula (I-S) and the compound of formula (I-R) by SMB chromatography under the following conditions:

Extract: 147.05 mL/min

Raffinate: 86.13 mL/min

Eluent: 183.18 mL/min

Feed: 50 mL/min

Recycling: 407.88 mL/min

Run Time: 0.57 min

Temperature: 25° C.

Pressure: 55 bar

The feed solution (25 g of compound of formula (I) in 1.0 L of mobile phase (25:75 (v:v) mixture of acetonitrile/methanol)) was injected continuously into the SMB system (Novasep Licosep Lab Unit), which was equipped with eight identical columns in 2-2-2-2 configuration containing 110 g (per column, 9.6 cm, 4.8 cm I.D.) of ChiralPAK-AD as stationary phase. The first eluting enantiomer (the compound of formula (I-R)) was contained in the raffinate stream and the second eluting enantiomer (the compound of formula (I-S)) was contained in the extract stream. The characterization data of the compound of formula (I-R) and the compound of formula (I-S) obtained from the SMB resolution were identical to those obtained above utilizing chiral HPLC.

The compound of formula (I) was resolved into the compound of formula (I-R) and the compound of formula (I-S) on a Waters preparative LCMS autopurification system. The first-eluting enantiomer from the chiral column was brominated (at a site well-removed from the stereogenic centre) to give the corresponding 5'-bromo derivative, which was subsequently crystallized to generate a single crystal suitable for X-ray crystallography. The crystal structure of this brominated derivative of the first-eluting enantiomer was obtained and its absolute configuration was found to be the same as the compound of formula (1-R). Hence, the second-eluting enantiomer from the chiral column is the compound of formula (1-S). Moreover, the material obtained from the extract stream of the SMB resolution had a specific optical rotation of the same sign (positive, i.e. dextrorotatory) as that of the material obtained from the aforementioned LC resolution.

Synthetic Example 4

Synthesis of 1'-{[3-(trifluoromethyl)pyridin-2-yl]methyl}-2,3-dihydrospiro[furo[2,3-g][1,4]benzodioxine-8,3'-indol]-2'(1'H)-one Compound of Formula (II)

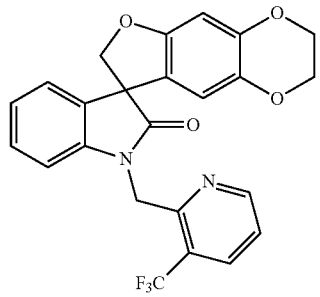 [SMILES: O=C1N(Cc2ncccc2C(F)(F)F)c2ccccc2C12COc1cc3c(cc12)OCCO3]

A 160 L reactor was charged with 1,4-dioxane (43 L) at ambient temperature followed by 2,3-dihydrospiro[furo[2,3-g][1,4]benzodioxine-8,3'-indol]-2'(1'H)-one (6.80 kg, 23 mol). To the resultant suspension was added cesium carbonate (18.7 kg, 58 mol) and the mixture was heated to 82° C. over 72 minutes. A container was rinsed with 1,4-diozane (7 L) and used for the addition of 2-(Chloromethyl)-3-(trifluoromethyl)pyridine hydrochloride (5.88 kg, 25 mol) portionwise over 35 minutes. The temperature of the reaction mixture was increased to 100° C. over 43 minutes and the mixture stirred at 100° C. for 3 h, cooled to 20° C. over 90 minutes and stirred for a further 16 h. Deionized water (40 L) and dichloromethane (40 L) were added and the resultant mixture stirred at 22° C. for 12 minutes. The stirring was stopped and the phases were allowed to separate for 21 minutes. The aqueous and organic phases were separated into drums. A 160 L reactor was charged with the aqueous phase and dichloromethane (41 L) was added. The mixture was stirred at 19° C. for 10 minutes, the stirring was stopped and the phases were allowed to separate for 10 minutes. The aqueous phase was removed and the organic phase from the previous step was transferred from the drum to the reactor. Deionized water (40 L) was added and the mixture stirred at 22° C. for 10 minutes. The stirring was stopped and the phases were allowed to separate for 43 minutes. The aqueous phase was removed and the organic phase concentrated to dryness under a reduced pressure of 712-97 mbar at 19-38° C. To the residue was added methanol (56 L) over 19 minutes. The resultant suspension was cooled to 3° C. over 64 minutes and stirred for 98 minutes. The mixture was filtered and the filter cake washed with cold (0° C.) methanol (14 L) and dried under a reduced pressure of 90-9 mbar at 21-46° C. for 10.5 h to obtain 1'-{[3-(trifluoromethyl)pyridin-2-yl]methyl}-2,3-dihydrospiro[furo[2,3-g][1,4]benzodioxine-8,3'-indol]-2'(1'H)-one (8.00 kg, 81%) as an off-white solid: purity (HPLC-UV) 99.8%; $^1$H NMR (300 MHz, CDCl$_3$) δ 8.67-8.63 (m, 1H), 8.01-7.96 (m, 1H), 7.35-7.28 (m, 1H), 7.22-7.13 (m, 2H), 7.05-6.98 (m, 1H), 6.63 (s, 1H), 6.62-6.58 (m, 1H), 6.49 (s, 1H), 5.42, 5.14 (ABq, J$_{AB}$=17.3 Hz, 2H), 5.00, 4.74 (ABq, J$_{AB}$=8.9 Hz, 2H), 4.22-4.10 (m, 4H); $^{13}$C NMR (75 MHz, CDCl$_3$) δ 178.3, 155.3, 152.5, 144.6, 142.4, 138.4, 134.3 (q, $^3$J$_{C-F}$=5.2 Hz), 132.8, 128.7, 124.4, (q, $^2$J$_{C-F}$=32.6 Hz), 123.9 (q, $^1$J$_{C-F}$=273.3 Hz), 123.8, 123.4, 122.2, 121.7, 112.6, 108.6, 99.2, 80.2, 64.6, 64.0, 58.3, 42.3 (q, $^4$J$_{C-F}$=3.3 Hz); MS (ES+) m/z 454.8 (M+1).

Synthetic Example 5

Resolution of Compound of Formula (II) by SMB Chromatography

The compound of formula (II) was resolved into the compound of formula (II-S) and the compound of formula (II-R) by SMB chromatography under the following conditions:
Extract: 182.67 mL/min
Raffinate: 67.44 mL/min
Eluent: 224.11 mL/min
Feed: 26.0 mL/min
Recycling: 420 mL/min
Run Time: 1.05 min
Temperature: 25° C.
Pressure: 50-55 bar The feed solution (68.4 g of compound of formula (II) in 1.0 L of mobile phase (97:3 (v:v) mixture of dichloromethane/acetone)) was injected continuously into the SMB system (Novasep Licosep Lab Unit), which was equipped with eight identical columns in 2-2-2-2 configuration containing 110 g (per column, 10.0 cm, 4.8 cm I.D.) of ChiralPAK®-IC as stationary phase. The compound of formula (II-R) was contained in the raffinate stream and the compound of formula (I-S) was contained in the extract stream.

A total of 10.62 kg of the compound of formula (II) were processed by SMB chromatography using the above conditions. All extract fractions with a chiral purity (HPLC)>99.0 a/a were pooled, concentrated to a volume of 26 L under reduced pressure and transferred to a 100 L reactor. The solution was further concentrated under a reduced pressure of 700-590 mbar at 26-37° C. until 13 L of distillate had been collected. Methanol (25 L) was added and the mixture concentrated under a reduced pressure of 650-360 mbar at 30-38° C. until 15 L of distillate had been collected. The mixture was cooled to 20° C. and methanol (15 L) was added. The mixture was concentrated under a reduced pressure of 650-320 mbar at 20-39° C. until 15 L of distillate had been collected and was cooled to 1° C. over 53 minutes and stirred for a further 70 minutes. The suspension was filtered and the filter cake was washed with cold (0° C.) methanol (9 L) and dried at ambient temperature under a flow of nitrogen gas for 15.5 h. The solid was further dried at a reduced pressure of 40-1 mbar at 50° C. for 195 minutes to afford the compound of formula (II-S), i.e., (S)-1'-{[3-(trifluoromethyl)pyridin-2-yl]methyl}-2,3-dihydrospiro[furo[2,3-g][1,4]benzodioxine-8,3'-indol]-2'(1'H)-one (3.62 kg) as a colorless solid: purity (HPLC-UV) 100%; $^1$H NMR (300 MHz, CDCl$_3$) δ 8.67-8.63 (m, 1H), 8.01-7.96 (m, 1H), 7.35-7.28 (m, 1H), 7.22-7.13 (m, 2H), 7.05-6.98 (m, 1H), 6.63 (s, 1H), 6.62-6.58 (m, 1H), 6.49 (s, 1H), 5.42, 5.14 (ABq, J$_{AB}$=17.3 Hz, 2H), 5.00, 4.74 (ABq, J$_{AB}$=8.9 Hz, 2H), 4.22-4.10 (m, 4H); $^{13}$C NMR (75 MHz, CDCl$_3$) δ 178.3, 155.3, 152.5, 144.6, 142.4, 138.4, 134.3 (q, $^3J_{C\text{-}F}$=5.2 Hz), 132.8, 128.7, 124.4, (q, $^2J_{C\text{-}F}$=32.6 Hz), 123.9 (q, $^1J_{C\text{-}F}$=273.3 Hz), 123.8, 123.4, 122.2, 121.7, 112.6, 108.6, 99.2, 80.2, 64.6, 64.0, 58.3, 42.3 (q, $^4J_{C\text{-}F}$=3.3 Hz); MS (ES+) m/z 454.8 (M+1); [α]$_D$+45.1° (c 2.02, DMSO); ee (CHIRALPAK IC, dichloromethane/acetone 97/3 (v/v)) 100%.

The compound of formula (II-R), i.e., (R)-1'-{[3-(trifluoromethyl)pyridin-2-yl]methyl}-2,3-dihydrospiro[furo[2,3-g][1,4]benzodioxine-8,3'-indol]-2'(1'H)-one, was isolated from the raffinate by standard procedures.

BIOLOGICAL ASSAYS

In order that the invention described herein may be more fully understood, the following biological assay is set forth to demonstrate the utility of the compounds prepared herein. It should be understood that this example is for illustrative purposes only and is not to be construed as limiting this invention in any manner.

Biological Example 1

Guanidine Influx Assay (In Vitro Assay)

This example describes an in vitro assay for testing and profiling test agents against human or rat voltage-gated sodium channels stably expressed in cells of either an endogenous or heterologously expressed origin. The assay is also useful for determining the IC$_{50}$ of a voltage-gated sodium channel modulating (preferably blocking) compound. The assay is based on the guanidine influx assay described by Reddy, N. L., et al., *J. Med. Chem.* (1998), 41(17):3298-302.

The guanidine influx assay is a radiotracer flux assay used to determine ion flux activity of voltage-gated sodium channels in a high-throughput microplate-based format. The assay uses $^{14}$C-guanidine hydrochloride in combination with various known voltage-gated sodium channel modulators that produce maintained influx, to assay the potency of test agents. Potency is determined by an IC$_{50}$ calculation. Selectivity is determined by comparing potency of the compound for the voltage-gated sodium channel of interest to its potency against other voltage-gated sodium channels (also called 'selectivity profiling').

Each of the test agents is assayed against cells that express the voltage-gated sodium channels of interest. Voltage-gated sodium channels are characterized as TTX sensitive or insensitive. This property is useful when evaluating the activities of a voltage-gated sodium channel of interest when it resides in a mixed population with other voltage-gated sodium channels. The following Table 1 summarizes cell lines useful in screening for a certain voltage-gated sodium channel activity in the presence or absence of TTX.

TABLE 1

| CELL LINE | mRNA Expression | Functional Characterization |
|---|---|---|
| CHO-K1 (Chinese Hamster Ovary; recommended host cell line) ATTC accession number CCL-61 | Na$_v$1.4 expression has been shown by RT-PCR No other Na$_V$ expression has been detected | The 18- to 20-fold increase in [$^{14}$C] guanidine influx was completely blocked using TTX. (Na$_V$1.4 is a TTX sensitive channel) |
| L6 (rat myoblast cell) ATTC Number CRL-1458 | Expression of Na$_v$1.4 and 1.5 | The 10- to 15-fold increase in [$^{14}$C] guanidine influx was only partially blocked by TTX at 100 nM (Na$_v$1.5 is TTX resistant) |
| SH-SY5Y (Human neuroblastoma) | Published Expression of Na$_V$1.9 and Na$_V$1.7 (Blum et | The 10- to 16-fold increase in [$^{14}$C] guanidine influx above |

TABLE 1-continued

| CELL LINE | mRNA Expression | Functional Characterization |
| --- | --- | --- |
| ATTC Number CRL-2266 | al.) | background was partially blocked by TTX (Na$_V$1.9 is TTX resistant) |
| SK-N-BE2C (a human neuroblastoma cell line ATCC Number CRL-2268) | Expression of Na$_V$1.8 | Stimulation of BE2C cells with pyrethroids results in a 6-fold increase in [$^{14}$C] guanidine influx above background. TTX partially blocked influx (Na$_V$1.8 is TTX resistant) |
| PC12 (rat pheochromocytoma) ATTC Number CRL-1721 | Expression of Na$_v$1.2 and Na$_V$1.7 | The 8- to 12-fold increase in [$^{14}$C] guanidine influx was completely blocked using TTX. (Na$_v$1.2 and Na$_V$1.7 are TTX sensitive channels) |
| HEK293 (human embryonic kidney) ATTC Number CRL-1573 | Expression of hNa$_V$1.7 | Na$_V$1.7 is a TTX sensitive channel. The TTX IC$_{50}$ in the functional Guanidinium assay is 8 nM. |

It is also possible to employ immortalized cell lines that heterologously express voltage-gated sodium channels. Cloning, stable transfection and propagation of such cell lines are known to those skilled in the art (see, for example, Klugbauer, N, et al., *EMBO J.* (1995), 14(6):1084-90; and Lossin, C., et al., *Neuron* (2002), 34, pp. 877-884).

Cells expressing the voltage-gated sodium channel of interest are grown according to the supplier or in the case of a recombinant cell in the presence of selective growth media such as G418 (Gibco/Invitrogen). The cells are disassociated from the culture dishes with an enzymatic solution (1×) Trypsin/EDTA (Gibco/Invitrogen) and analyzed for density and viability using haemocytometer (Neubauer). Disassociated cells are washed and resuspended in their culture media then plated into Poly-D-Lysine coated Scintiplates (Perkin Elmer) (approximately 100,000 cells/well) and incubated at 37° C./5% CO$_2$ for 20-24 hours. After an extensive wash with Low sodium HEPES-buffered saline solution (LNHBSS) (150 mM Choline Chloride, 20 nM HEPES (Sigma), 1 mM Calcium Chloride, 5 mM Potassium Chloride, 1 mM Magnesium Chloride, 10 mM Glucose) the test agents are diluted with LNHBSS and then added to each well at the desired concentration. (Varying concentrations of test agent may be used). The activation/radiolabel mixture contains an alkaloid such as veratridine or Aconitine (Sigma) or a pyrethroid such as deltamethrin, venom from the scorpion *Leiurus quinquestriatus hebraeus* (Sigma) and $^{14}$C-guanidine hydrochloride (ARC) to measure flux through the voltage-gated sodium channels.

After loading the cells with test agent and activation/radiolabel mixture, the Poly-D-Lysine coated Scintiplates are incubated at ambient temperature. Following the incubation, the Poly-D-Lysine coated Scintplates are extensively washed with LNHBSS supplemented with Guanidine (Sigma). The Poly-D-Lysine coated Scintiplates are dried and then counted using a Wallac MicroBeta TriLux (Perkin-Elmer Life Sciences). The ability of the test agent to block voltage-gated sodium channel activity is determined by comparing the amount of $^{14}$C-guanidine present inside the cells expressing the different voltage-gated sodium channels. Based on this data, a variety of calculations, as set out elsewhere in this specification, may be used to determine whether a test agent is selective for a particular voltage-gated sodium channel.

The IC$_{50}$ value of a test agent for a specific voltage-gated sodium channel may be determined using the above general method. The IC$_{50}$ may be determined using a 3, 8, 10, 12 or 16 point curve in duplicate or triplicate with a starting concentration of 1, 5 or 10 µM diluted serially with a final concentration reaching the sub-nanomolar, nanomolar and low micromolar ranges. Typically the mid-point concentration of test agent is set at 1 µM, and sequential concentrations of half dilutions greater or smaller are applied (e.g., 0.5 µM; 5 µM and 0.25 µM; 10 µM and 0.125 µM; 20 µM etc.). The IC$_{50}$ curve is calculated using the 4 Parameter Logistic Model or Sigmoidal Dose-Response Model formula (fit=(A+((B−A)/(1+((C/x)^D)))).

The fold selectivity, factor of selectivity or multiple of selectivity, is calculated by dividing the IC$_{50}$ value of the test voltage-gated sodium channel by the reference voltage-gated sodium channel, for example, Na$_V$1.5.

Accordingly, the compounds prepared by the methods disclosed herein demonstrated voltage-gated sodium channel blocking activity against hNa$_V$1.7 as set forth below in Table 2:

TABLE 2

| Compound | Chemical Name | IC$_{50}$ (µM) |
| --- | --- | --- |
| (I) | 1'-{[5-(trifluoromethyl)furan-2-yl]methyl}spiro[furo[2,3-f][1,3]benzodioxole-7,3'-indol]-2'(1'H)-one | 0.007 |
| (I-R) | (R)-1'-{[5-(trifluoromethyl)furan-2-yl]methyl}spiro[furo[2,3-f][1,3]benzodioxole-7,3'-indol]-2'(1'H)-one | 4.200 |
| (I-S) | (S)-1'-{[5-(trifluoromethyl)furan-2-yl]methyl}spiro[furo[2,3-f][1,3]benzodioxole-7,3'-indol]-2'(1'H)-one | 0.003 |
| (II) | 1'-{[3-(trifluoromethyl)pyridin-2-yl]methyl}-2,3-dihydrospiro[furo[2,3-g][1,4]benzodioxine-8,3'-indol]-2'(1'H)-one | 0.015 |
| (II-S) | (S)-1'-{[3-(trifluoromethyl)pyridin-2-yl]methyl}-2,3-dihydrospiro[furo[2,3-g][1,4]benzodioxine-8,3'-indol]-2'(1'H)-one | 0.005 |

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of preparing a compound of formula (II):

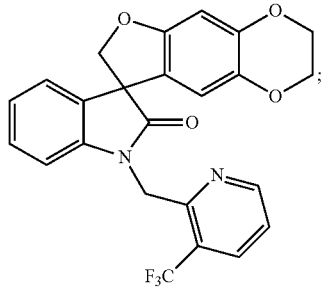
(II)

or a pharmaceutically acceptable salt thereof, as a single stereoisomer or enantiomer or a mixture thereof;
wherein the method comprises:
a) treating a compound of formula (14):

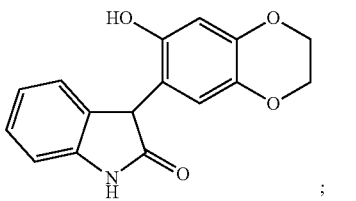
(14)

or a pharmaceutically acceptable salt thereof, with an alkylating agent under suitable conditions to form a compound of formula (15):

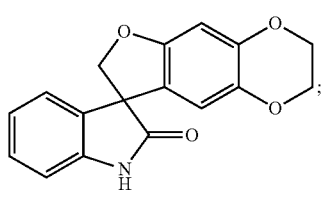
(15)

or a pharmaceutically acceptable salt thereof; and
b) treating the compound of formula (15), or a pharmaceutically acceptable salt thereof, with a compound of formula (16):

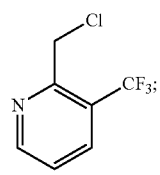
(16)

or a pharmaceutically acceptable salt thereof, under suitable conditions to provide the compound of formula (II), or a pharmaceutically acceptable salt thereof, as a single stereoisomer or enantiomer or a mixture thereof.

2. The method of claim 1 further comprising a preparation of the compound of formula (14), or a pharmaceutically acceptable salt thereof, wherein the method comprises treating a compound of formula (13):

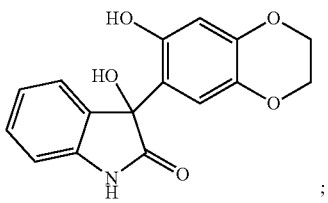
(13)

or a pharmaceutically acceptable salt thereof, under suitable conditions to form the compound of formula (14), or a pharmaceutically acceptable salt thereof.

3. The method of claim 2 further comprising a preparation of the compound of formula (13), or a pharmaceutically acceptable salt thereof, wherein the method comprises:
c) reacting a compound of formula (12):

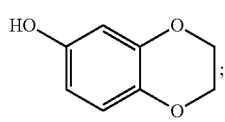
(12)

with a Grignard reagent of formula (3):

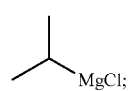
(3)

under suitable conditions to form an intermediate product; and
d) reacting the intermediate product of c) with a compound of formula (I):

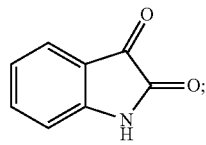
(1)

or a pharmaceutically acceptable salt thereof, under suitable conditions to form the compound of formula (13), or a pharmaceutically acceptable salt thereof.

4. The method of claim 3 further comprising a preparation of the compound of formula (12), or a pharmaceutically acceptable salt thereof, wherein the method comprises treating a compound of formula (II):

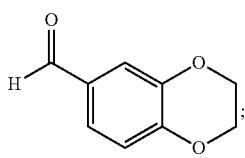
(11)

with an oxidizing agent under suitable conditions to form the compound of formula (12), or a pharmaceutically acceptable salt thereof.

5. The method of claim 4 further comprising a preparation of the compound of formula (II), wherein the method comprises treating a compound of formula (10):

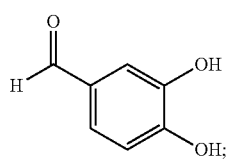
with a suitable alkylating reagent under suitable conditions to form the compound of formula (II).
6. The method of claim 1 further comprising resolving a compound of formula (II) under suitable conditions to yield a compound of formula (II-S):
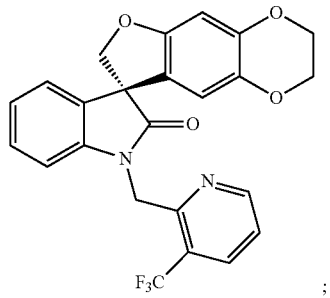
or a pharmaceutically acceptable salt thereof; and a compound of formula (II-R):
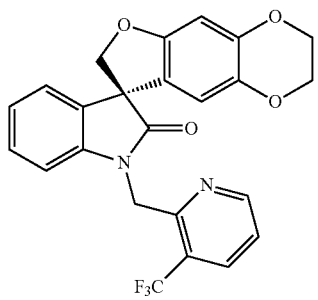
or a pharmaceutically acceptable salt thereof.
* * * * *